(12) United States Patent
Arnold et al.

(10) Patent No.: US 10,292,581 B2
(45) Date of Patent: May 21, 2019

(54) DISPLAY DEVICE FOR DEMONSTRATING OPTICAL PROPERTIES OF EYEGLASSES

(71) Applicants: Carl Zeiss Vision International GmbH, Aalen (DE); Carl Zeiss AG, Oberkochen (DE)

(72) Inventors: Manfred Arnold, Aalen (DE); Marion Kupfer, Waiblingen (DE); Martin Brandl, Aalen (DE); Michael Stefan Rill, Jena (DE); Johannes Kindt, Weimar (DE); Karsten Lindig, Erfurt (DE); Jesús-Miguel Cabeza-Guillén, Aalen (DE)

(73) Assignees: Carl Zeiss Vision International GmbH, Aalen (DE); Carl Zeiss AG, Oberkochen (DE)

( * ) Notice: Subject to any disclaimer, the term of this patent is extended or adjusted under 35 U.S.C. 154(b) by 0 days.

(21) Appl. No.: 15/462,810

(22) Filed: Mar. 18, 2017

(65) Prior Publication Data

US 2017/0188813 A1    Jul. 6, 2017

Related U.S. Application Data

(63) Continuation of application No. PCT/EP2015/068541, filed on Aug. 12, 2015.

(30) Foreign Application Priority Data

Sep. 22, 2014  (DE) .................. 10 2014 113 680
Nov. 14, 2014  (DE) .................. 10 2014 116 665
Jan. 8, 2015    (DE) .................. 10 2015 100 147

(51) Int. Cl.
*A61B 3/04*    (2006.01)
*A61B 3/10*    (2006.01)
(Continued)

(52) U.S. Cl.
CPC .............. *A61B 3/032* (2013.01); *A61B 3/005* (2013.01); *A61B 3/0008* (2013.01);
(Continued)

(58) Field of Classification Search
CPC .. A61B 3/04; A61B 3/103; A61B 3/14; A61B 3/152; A61B 3/113; A61B 3/1225;
(Continued)

(56) References Cited

U.S. PATENT DOCUMENTS 6,692,127 B2    2/2004  Abitbol et al.
7,338,165 B2    3/2008  Dai
(Continued)

FOREIGN PATENT DOCUMENTS

DE    10153397 A1        5/2003
DE    102008012268 A1    9/2009
(Continued)

OTHER PUBLICATIONS

M. Vu: "Simulation of Vision through an Actual Human Optical System," Masters Thesis, University of California, Berkley submitted in the Fall of 2001.
(Continued)

*Primary Examiner* — Dawayne Pinkney
(74) *Attorney, Agent, or Firm* — Ewers & Hasselmann PLLC

(57) ABSTRACT

A display device with a retaining device is disclosed, which can be placed on the head of a user. The display device contains a first image generator, which is secured or can be secured to the retaining device, and a first optical imaging system which is secured to the retaining device and which is designed to image an image generated on a first image plane (E) by the first image generator such that the user can perceive the image with a first eye (LA) when the retaining device is placed on the head of the user. The retaining device (Continued)

supports a first refraction determining optical system which is designed to determine the subjective refraction of the first eye (LA) when the retaining device is placed on the head of the user and/or the first optical imaging system is configured to be variable.

27 Claims, 7 Drawing Sheets

(51) Int. Cl.
| | |
|---|---|
| A61B 3/02 | (2006.01) |
| A61B 3/00 | (2006.01) |
| A61B 3/032 | (2006.01) |
| A61B 3/103 | (2006.01) |
| G02C 7/02 | (2006.01) |
| A61B 3/14 | (2006.01) |
| A61B 3/06 | (2006.01) |
| A61B 3/11 | (2006.01) |
| A61B 5/00 | (2006.01) |
| A61B 3/113 | (2006.01) |

(52) U.S. Cl.
CPC .......... *A61B 3/0025* (2013.01); *A61B 3/0041* (2013.01); *A61B 3/04* (2013.01); *A61B 3/063* (2013.01); *A61B 3/103* (2013.01); *A61B 3/112* (2013.01); *A61B 3/113* (2013.01); *A61B 3/14* (2013.01); *A61B 5/6898* (2013.01); *G02C 7/024* (2013.01); *G02C 7/028* (2013.01); *A61B 3/10* (2013.01)

(58) Field of Classification Search
CPC ....... A61B 3/024; A61B 3/032; A61B 3/0285; A61B 3/18; A61B 3/1015; A61H 5/00
USPC ........ 351/228, 200, 203, 205–206, 208–210, 351/216, 221–223, 227, 230–231, 351/233–234, 236, 240, 245–246
See application file for complete search history.

(56) References Cited

U.S. PATENT DOCUMENTS

| | | | |
|---|---|---|---|
| 7,914,148 B2 | 3/2011 | Fisher et al. | |
| 8,226,238 B2 | 7/2012 | Spratt | |
| 8,820,931 B2 | 9/2014 | Walsh et al. | |
| 9,364,142 B2 | 6/2016 | Hatanaka | |
| 2003/0108350 A1 | 6/2003 | Brauning | |
| 2004/0032568 A1 | 2/2004 | Fukuma et al. | |
| 2005/0018134 A1* | 1/2005 | Noda | A61B 3/132 351/205 |
| 2006/0110008 A1 | 5/2006 | Vertegaal et al. | |
| 2007/0200927 A1 | 8/2007 | Krenik | |
| 2008/0316427 A1 | 12/2008 | Fisher et al. | |
| 2009/0153796 A1 | 6/2009 | Rabner | |
| 2010/0283969 A1 | 11/2010 | Cooperstock et al. | |
| 2012/0026183 A1 | 2/2012 | Qi et al. | |
| 2012/0194781 A1* | 8/2012 | Agurok | G02C 7/081 351/201 |
| 2012/0212598 A1 | 8/2012 | Mowrey et al. | |
| 2013/0027668 A1 | 1/2013 | Pamplona et al. | |
| 2013/0222764 A1* | 8/2013 | Thompson | A61B 3/103 351/209 |
| 2013/0235346 A1 | 9/2013 | Huang et al. | |
| 2015/0163480 A1 | 6/2015 | Qi et al. | |
| 2017/0172406 A1* | 6/2017 | Pamplona | A61B 3/028 |

FOREIGN PATENT DOCUMENTS

| | | |
|---|---|---|
| DE | 102009008876 A1 | 9/2010 |
| DE | 202011103183 U1 | 11/2011 |
| DE | 102014107938 A1 | 12/2015 |
| DE | 102014017534 A1 | 5/2016 |
| EP | 1308128 A2 | 5/2003 |
| EP | 2341388 A1 | 7/2011 |
| EP | 2363058 A1 | 7/2014 |
| EP | 2856931 B1 | 4/2015 |
| EP | 2 886 040 A1 | 6/2015 |
| JP | 3893760 B2 | 3/2007 |
| WO | 01/88654 A2 | 11/2001 |
| WO | 2004/112576 A2 | 12/2004 |
| WO | 2007/056795 A1 | 5/2007 |
| WO | 2010/117386 A1 | 10/2010 |
| WO | 2013/175923 A1 | 11/2013 |
| WO | 2014/030403 A1 | 2/2014 |

OTHER PUBLICATIONS

Wikipedia Article "Bestimmung der subjektiven Refraktion," (de.wikipedia.org/wiki/Refraktion#Bestimmung_der_subjektiven_Refraktion) and English language counterpart article available online at least as of Jul. 9, 2015.
Product description: "Un casque 3D en magasin pour mieux démontrer les bénéfices des verres, signé Essilor," (http://www.acuite.fr/actualite/produit/76619/un-casque-3d-en-magasin-pour-mieux-demontrer-les-benefices-des-verres-signe) and English-language machine translation thereof, published online Jul. 7, 2015.
Office Action of the German Patent and Trademark Office dated Jun. 26, 2015 (Priority Application No. DE 10 2014 116 665.5) and English-language translation thereof.
Office Action of the German Patent and Trademark Office dated Jun. 30, 2015 (Priority Application No. DE 10 2015 100 147.0) and English-language translation thereof.
International Search Report of the European Patent Office dated Nov. 3, 2015 and English-language translation thereof.
International Preliminary Report of Patentability of the European Patent Office dated Nov. 23, 2016 and English-language translation thereof.
Office action of the European Patent Office in EP 15 747 829.8, which is a counterpart application of this application, dated Sep. 29, 2017, and English-language translation thereof.
Office action of the European Patent Office in EP 15 747 829.8, which is a counterpart application of this application, dated Apr. 26, 2018, and English-language translation thereof.

* cited by examiner

DISPLAY DEVICE FOR DEMONSTRATING OPTICAL PROPERTIES OF EYEGLASSES

CROSS REFERENCE TO RELATED APPLICATIONS

This application is a continuation application of International Application No. PCT/EP2015/068541 filed on Aug. 12, 2015, and claims priority to German patent applications DE 10 2014 113 680.2 filed on Sep. 22, 2014, DE 10 2014 116 665.5 filed on Nov. 14, 2014, and DE 10 2015 100 147.0 filed on Jan. 8, 2015, all of which are hereby incorporated by reference in their entireties as if fully set forth herein.

TECHNICAL FIELD

The invention relates to a display device having a holding device which can be placed onto the head of a user and including an image generator that is arranged in a predetermined position in relation to the holding device. The display device is suitable for demonstrating optical properties of spectacle lenses. Furthermore, the invention relates to a system including an image generator and a holding device, which can be placed onto the head of a user. An imaging optical unit is secured to the holding device and designed to image an image generated by the image generator in an image plane (E), such that a user can perceive the image with a first eye (LA) when the holding device is placed on the head of the user.

BACKGROUND

An ophthalmologist or optician measures the eye and determines visual acuity. The demonstration of different variants in words is difficult and depends greatly on the explanation ability of the optician, the comprehension of the spectacle lens customer, and the given time. Without actually implementing spectacles of the recommended type, however, they cannot actually be demonstrated. Sometimes progressive spectacle lenses are classified as "incompatible" by the user. However, upon being measured again, these lenses prove to conform to the spectacle lens prescription and the user is satisfied only after choosing a different design. Thus, there is a need for objectification in the consultation and dispensing process for spectacles.

JP 3 893 760 A1 discloses the simulation of the visual impression of a wearer of spectacles or the generation of a virtual visual impression of a wearer of spectacles. For this purpose, an image on the retina of the wearer of spectacles is simulated on the basis of an original image and displayed. In particular, the movement of the image when gazing through a progressive lens taking account of head movements is also simulated.

EP 2 341 388 A1 describes a development of the simulation described in JP 3 893 760 A1 which takes account of the viewing direction of the wearer of spectacles and thus the change in the intersection point of the visual line—assigned to the viewing direction—from the eye through the progressive lens with respect to the original image. The simulation and display are carried out separately for each eye of the wearer of spectacles.

EP 2 856 931 A1 reveals a further development of the simulations described in the documents JP 3 893 760 A1 and EP 2 341 388 A1. Instead of an original image recorded beforehand, cameras assigned to the respective eyes and distance sensors aligned in the optical axial direction of the cameras are provided. The viewing direction of the wearer of spectacles controls the alignment of the cameras and distance sensors. The images recorded by the cameras are used together with the distances of the object recorded by the cameras, the distances being determined by the distance sensors, instead of the abovementioned original image as input variables for the simulation. The display is carried out on a so-called head-mounted display that is incorporated into the same carrier for the cameras and the distance sensors.

WO 2007/056795 A1 discloses an arrangement similar to that described in EP 2 856 931 A1. In particular, a head-mounted spectacle lens simulator is described therein. The head-mounted spectacle lens simulator comprises—depending on the embodiment as a mono or stereo image simulator—one or two cameras that record the scenery of the wearer before or during the simulation. The simulation can take account of the imaging aberrations of the subject's eye that are measured by a wavefront sensor. Furthermore or alternatively, the simulation can take account of the head and/or eye movements recorded by corresponding head and/or eye movement detectors, so-called head and/or eye trackers. The simulation can furthermore include the spectacle lens design, i.e., the optical properties of the spectacle lens for the observer depending on the respective viewing point through the computationally represented spectacle lens. Single-vision lenses, bifocal lenses or progressive lenses may be involved. The simulation can also include the frame size of the respective spectacle lenses. Finally, besides the visual impression on the basis of head movements and different viewing directions through the respective spectacle lens, it is also possible to superimpose areas or lines on the scenery represented for the observer in order to illustrate for the observer zone boundaries, such as e.g., near and distance regions and progression channel in the case of a progressive lens.

DE 10 2009 008 876 A1 describes a visual impression simulation unit for simulating and displaying the person's actual visual impression on the basis of measured refraction errors of an eye of a person and prescription values determined therefrom. The visual impression simulation unit may operate e.g., according to one of the methods described in the MSc thesis by Woojin Matthew Vu "Simulation of Vision through an Actual Human Optical System," in 2001 at the University of California, Berkley, USA or WO 2004/112576 A2. Both documents describe methods as to how the visual impression can be simulated on the basis of wavefront data. In this regard, e.g., the prescription values determined in the preceding step are subtracted from the measured wavefront and the visual impression is simulated by convolving the residual wavefront with a suitable test image.

WO 01/88654 A2 reveals a computer configured to display on a screen the visual impression of a wearer of spectacles when gazing through a plurality of different spectacle lenses. In particular, the document reveals the representation of a scene which the wearer of spectacles would perceive when gazing through photochromic spectacle lenses under different weather conditions. Furthermore, a description is given of gazing through tinted spectacle lenses, bifocal and progressive spectacle lenses, scratch-resistant spectacle lenses, and antireflection-coated spectacle lenses.

During the technical trade fair for spectacles Silmo 2015, the presentation of a head-mounted display (HMD) was announced, which purportedly is able to display three-dimensionally the visual impression through different spectacle lenses for the wearer of spectacles. The presentation can be found at www.acuite.fr/actualite/produit/76619/uncasque-3d-en-magasin-pour-mieux-demontrer-les-benefices-des-verres-signe?utm_campaign=ecAcuite&utm_medium=flashoptic&utm_source=flashoptic (last accessed Jul. 9, 2015). However, the functioning of this device is not described therein.

DE 10 2014 107 938 A1, reveals a display device in the form of an HMD comprising a holding device which can be placed onto the head of a user, and comprising a first imaging optical unit secured to the holding device and designed to image an image generated in an image plane as a virtual image such that the user can perceive the image with a first eye when the holding device is in the state placed on the head.

The display device may have a second imaging optical unit for the observer's second eye, which is preferably structurally identical to the first imaging optical unit. In this case, this is also referred to as a stereo image observer.

The first imaging optical unit of the display device according to DE 10 2014 107 938 A1 has a first lens having negative refractive power and a second lens having positive refractive power, the second lens being spaced apart from the first lens. The first lens is positioned nearer to the image plane than the second lens. An image generator is arranged in the image plane and generates the image that is imaged by means of the first imaging optical unit. The image generator is arranged in an exchangeable fashion in the image plane.

DE 10 2014 017 534 A1 describes a display device similar to the display device as described in DE 10 2014 107 938 A1. This display device comprises a holding device which can be placed onto the head of a user, and a first imaging optical unit secured to the holding device and designed to image an image generated in an image plane as a virtual image such that the user with the holding device placed onto the head can perceive the image with a first eye. In a departure from the embodiment according to DE 10 2014 107 938 A1, the first imaging optical unit has as imaging element exactly one first lens having a first and a second interface. The two interfaces are curved aspherically in each case. As in the embodiment described previously, an image generator is arranged in the image plane and generates the image that is imaged by means of the first imaging optical unit. The image generator in that case is arranged in an exchangeable fashion in the image plane.

With regard to subjective refraction determination, according to de.wikipedia.org/wiki/Refraktion#Bestimmung_der_subjektiven_Refraktion (last accessed on Jul. 9, 2015) it is known in the art to position in front of the person to be examined successively systematically different lenses, so-called measuring spectacle lenses, and to ask about an improvement or deterioration in the visual impression. In this case, such visual symbols which are also used for determining visual acuity are generally offered as objects for observation. The process of selecting the measuring spectacle lenses and positioning them in front of a person is greatly accelerated by the use of a phoropter, an apparatus that can be used to switch back and forth rapidly between different measuring spectacle lenses. It is also possible to use "measuring spectacles" for this procedure. Determination is continued until no further improvement of visual acuity is obtained by varying the correction values offered. The optical power of the measuring spectacle lenses thus selected, taking account of the examination distance, is then the subjective refraction.

EP 2 363 058 B1 discloses a subjective refraction determining device comprising two lenses. The first lens comprises a plurality of adjacent first zones arranged over the lens in a first direction, wherein each first zone has a different average power. A plurality of adjacent second zones are arranged over the first lens in a second direction perpendicular to the first direction, wherein each second zone has a different cylinder power. The first zones arranged over the first lens in the first direction overlap the second zones arranged over the first lens in the second direction. Both the average power and the cylinder power vary across the first lens by four diopters or more. The second lens has a constant average power arranged relative to the lens such that an observer can observe a target through the second lens and the lens having the varying average power and the varying cylinder power.

Although the above-described devices in which the visual impression of a wearer of spectacles is displayed by simulation have fundamentally proved worthwhile for demonstrating optical properties of spectacle lenses, there is a need for a simple demonstration device.

SUMMARY

An object of the invention therefore is to provide a comparably simple display device which is suitable for demonstrating optical properties of spectacle lenses by modifying a mono or stereo image observer of the generic type.

As already explained above, the display device disclosed herein is based on a mono or stereo image observer. Such an image observer constitutes a display device including a holding device which can be placed onto the head of a user. Either the holding device has a receptacle for a first image generator or the first image generator is already secured, if appropriate in a releasable fashion, to the holding device. Furthermore, a first imaging optical unit is secured to the holding device. The imaging optical unit is designed and configured to image an image generated by the first image generator in a first image plane as a virtual image such that the user can perceive the image with a first eye when the holding device is in the state placed on the head.

In a departure from the related art described above, the invention now provides for the holding device to carry a first refraction determining optical unit designed for determining the subjective refraction of the first eye when the holding device is in the state placed on the head.

Alternatively or additionally, the first imaging optical unit may be designed to be variable. In particular, the first imaging optical unit may be designed to be variable externally in terms of its optical power (sphere, astigmatism and the orientation thereof).

The purpose of the refraction determining optical unit is to compensate for the refraction deficit, in particular the spherical and cylindrical power errors. Accordingly, the refraction determining optical unit serves to demonstrate to the user the correction of his/her new spectacles.

A purpose of the variable first imaging optical unit is, in particular, to vary the location of the focus of the imaging optical unit in order thereby bring about for example an accommodation effort corresponding to the envisaged new spectacles for the user. Accordingly, like the refraction determining optical unit described above, the first imaging optical unit serves to demonstrate to the user the correction of his/her new spectacles including the individual suitability for near vision taking account of the accommodation capability of the user.

An object of the invention is accordingly achieved in its entirety by the use of at least one of these optical elements, namely the first refraction determining optical unit or the variable configuration of the first imaging optical unit.

In one exemplary embodiment of the invention, the first imaging optical unit may be designed to be variable by virtue of the fact that the first imaging optical unit has at least one lens which is designed to be displaceable perpendicularly to the first image plane. Alternatively or additionally, the first imaging optical unit may have at least one lens which is designed to be rotatable and/or displaceable parallel to the first image plane. It is also possible for a lens to be designed to be rotatable and/or displaceable both in a perpendicular direction with respect to the first image plane and parallel to the first image plane.

By displacing a lens of the first imaging optical unit in the direction of the surface normal of the first image plane, there is a shift in the focus of the first imaging optical unit in the direction of the surface normal. By displacing and/or rotating a lens of the first imaging optical unit parallel to the first image plane, there is a shift in the focus of the first imaging optical unit in the plane which is parallel to the first image plane and in which the focus was originally situated.

All of the measures described above have the effect that the user's eye must adjust to the new focus position by changing its accommodation.

Additionally or alternatively, it is also possible that the first imaging optical unit or a lens of the first imaging optical unit can be tilted. The inclination of the first imaging optical unit or of the lens of the first imaging optical unit changes as a result. By virtue of this measure, it is possible to demonstrate a prismatic effect which can be used for compensating for a prismatic refraction deficit.

One exemplary embodiment of the invention provides for the first refraction determining optical unit to comprise one or a plurality of exchangeable measuring spectacle lenses. The latter may be constructed similarly to the measuring spectacle lenses of the precision measuring spectacles from ZEISS®. The holding device may have corresponding mounts for this purpose. The task of the measuring spectacle lenses is to carry out for the user an adaptation such that the user can see sharply image points that are apparently at infinity, that is to say that the user's refraction deficit, measurable in terms of sphere, cylinder, and associated axis, is thereby compensated for. The measuring lenses are spherical, toric or cylindrical single-vision lenses having a relatively small diameter of 2 to 2.5 cm which are arranged at a relatively close distance, namely 10 to 15 mm, from the corneal vertex and therefore nevertheless ensure a sufficiently large field of view. The measuring spectacle lenses demonstrate to the observer the correction of his/her new spectacles in terms of distance.

If the user has a refraction deficit both in spherical power and in cylindrical power, e.g., a spherical measuring spectacle lens for the correction of the spherical portion of the refraction deficit and a cylindrical measuring spectacle lens for the correction of the cylindrical portion of the refraction deficit may be arranged one behind the other in the viewing direction of the user. The measuring spectacle lens having cylindrical power may be embodied such that it is rotatable e.g., about its center axis in order to vary the axial position.

Two measuring spectacle lenses having cylindrical or toric power may also be arranged one behind the other in the viewing direction of the observer, the lenses being rotatable about a common axis by adjustable angles in order to compensate for the subject's astigmatism including the orientation thereof.

Alternatively, that is to say instead of the measuring spectacle lenses, the first refraction determining optical unit may also comprise a lens having a plurality of adjacent first and second zones. The adjacent first zones are arranged over the lens in a first direction. Each first zone has a different average power. A plurality of adjacent second zones are arranged over the first lens in a second direction perpendicular to the first direction. Each second zone has a different cylinder power. The first zones arranged over the first lens in the first direction overlap the second zones arranged over the first lens in the second direction. The lens is designed to be rotatable and/or displaceable parallel to the first image plane. Furthermore, the refraction determining optical unit may have, in addition to the first lens, a further lens having a constant average power, which is arranged relative to the first lens such that the observer can observe a target through the further lens and the first lens, which has a varying average power and a varying cylinder power.

One exemplary embodiment of the invention is the first image generator being arranged in an exchangeable fashion in the first image plane. By way of example, a smartphone may be used as image generator. This exemplary embodiment is distinguished by its comparatively simple mechanical construction and cost-effective producibility.

In a further exemplary embodiment of the invention, a second imaging optical unit designed to be variable can be secured to the holding device, the second imaging optical unit being designed to image the image generated in the first image plane or an image generated by a second image generator in a second image plane such that the user can perceive the image with the second eye when the holding device is in the state placed on the head.

A further configuration as an alternative to the aforementioned further exemplary embodiment of the invention provides for the holding device to carry a second refraction determining optical unit designed for determining the subjective refraction of the second eye when the holding device is placed on the head.

While it is thus possible in principle to embody the display device according to the invention in a monocular fashion, the further configuration and the alternative further configuration are examples of binocular or stereoscopic variants. Accordingly, the visual impression which the observer would have with his/her new spectacles can be demonstrated to the observer for both eyes simultaneously.

In this case, it is expedient if the first imaging optical unit and the second imaging optical unit are designed complementarily to one another and/or if the first refraction determining optical unit and the second refraction determining optical unit are designed complementarily to one another. In the context of the present invention, complementary design should be understood to mean a symmetry in a functional regard. The first and second imaging optical units, on the one hand, and the first and second refraction determining optical units, on the other hand, are intended to be constructed functionally identically, but they are intended to be designed to be operable separately for the right and left eyes. Since the right and left eyes of a user themselves are neither functionally nor structurally symmetrical in their embodiment, with consideration being given e.g. to the convergence movement of the eyes, during near vision, the corresponding imaging and/or refraction optical units for the right and left eyes need not be designed identically. A symmetrical design with respect to a plane arranged centrally between the two corresponding optical units for the right and left eyes is desirable, however.

With the aid of the first image generator, respectively separate test image impressions for the right and left eyes can be presented to the user during the demonstration of the optical properties of spectacle lenses. Owing to the use of the two imaging optical units assigned separately to the respective eyes, the display device acts like a stereo image observer.

One embodiment variant of the display device according to the invention provides for an orientation sensor for determining the orientation of the holding device to be mounted on the holding device. Alternatively or additionally, a motion sensor for determining the movement of the holding device may also be secured to the holding device. Finally, likewise additionally or alternatively, an inclination sensor for determining the inclination of the holding device may be mounted on the holding device. The head position and/or movement of the head of the user can be determined with the aid of the orientation, motion, and/or inclination sensors. This information can be used for changing the content of the virtual image by changing the content of the image in the first image plane and/or changing the state of the first/second imaging optical unit and/or changing the state of the first/second refraction optical unit. Exemplary embodiments in this respect are described in greater detail below. These measures all serve for demonstrating the optical properties of spectacles not yet existing in reality for the user. In particular, the virtual image content can be varied such that the user's visual impression for both eyes is demonstrated in the best possible way with the spectacle lens to be demonstrated, with the inclusion of the movements of the head.

In one particularly advantageous configuration of the invention, the display device may have a simulation unit for simulating the effect of a gaze of the first eye of the user through a spectacle lens to be demonstrated for the first eye and for outputting the simulation of the effect of the gaze of the first eye of the user through the spectacle lens to be demonstrated for the first eye in the form of one image in the first image plane by means of the first image generator. Alternatively or additionally, provision may be made of a simulation unit for simulating the effect of a gaze of the second eye of the user through a spectacle lens to be demonstrated for the second eye and for outputting the simulation of the effect of the gaze of the second eye of the user through the spectacle lens to be demonstrated for the second eye in the form of one image in the first image plane by means of the first image generator or in the form of one image in the second image plane by means of the second image generator. The two simulation units may also be part of a single device.

In particular, one or both simulation units may be realized in the form of a computer on which software is operated for implementing the functionalities described. The computer may be embodied as a unit separate from the above-described parts or components of the display device which is held by the holding device. However, the computer may also be the processor or the central processing unit of the above-described smartphone on which runs an application program or application software (so-called mobile app) that carries out the simulation described above. In this case, the smartphone provides not only the first image generator in the form of its screen, but also the simulation unit(s) for the computational generation of an image for one or both eyes or of two separate images for each eye, which represents or represent the visual impression when gazing through a corresponding spectacle lens or spectacles comprising two spectacle lenses. To put it another way, the app calculates test image impressions mathematically whilst simulating the effect of the gaze of the user through spectacles to be demonstrated comprising spectacle lenses to be demonstrated. This mathematical simulation offers that test image which, for the user, taking account of the measuring spectacle lenses mounted on the stereo image observer for rectifying the refraction deficit, gives rise to the best possible visual impression which would arise if the spectacle lens likewise taken as a basis in the simulation were actually worn by the user in the intended position in front of his/her eyes.

The test image displayed on the first image generator and, if appropriate, on the second image generator or the test images displayed on the first image generator and, if appropriate, on the second image generator may clarify e.g., the distortion of the eye-spectacle lens system. It is possible for the test image or the test images to demonstrate the blur of individual viewing directions that is generated by the astigmatism of oblique beams through one progressive lens (one eye) or two progressive lenses (two eyes). It is also possible for the test image or test images to show the vertical prismatic secondary effects occurring for both eyes in the case of the individual viewing directions of progressive lenses. Furthermore, it is possible for the test image or test images to illustrate the effect of a polarizing spectacle lens in different use situations. Finally, it is possible to display the darkening and lightening behavior of phototropic spectacle lenses in different use situations on the test image or test images. Furthermore, the test image or test images can reproduce the effect of a spectacle lens or of spectacles in different lighting conditions and/or in different use situations. Furthermore, the influence of different spectacle lens materials and/or coatings of the spectacle lens can be demonstrated. All the above-described possibilities for simulation and generation of test images may take account of the size and shape of the respective spectacle lens, and also the influence of size and shape of near part, distance part, if appropriate intermediate part, and if appropriate progression channel, on the imaging properties of multifocal lenses. It is furthermore possible to displace the test images for the right and left eyes relative to one another in order thus to demonstrate the effect of prismatic spectacle lenses. The test images for the right and left eyes may, if appropriate, also be scaled by software to demonstrate the effect of the inherent magnification of spectacle lenses. It is also possible to take account of the pupillary distance when generating the test images. By way of example, a presetting effected by the advising service provider may be used for this purpose.

A further very advantageous exemplary embodiment of the invention provides for the simulation unit for simulating the effect of a gaze of the first eye to be designed to take account of the orientation determined by the orientation sensor and/or the movement determined by the motion sensor and/or the inclination determined by the inclination sensor in the simulation of the effect of the gaze of the first eye of the user through the spectacle lens to be demonstrated for the first eye. Alternatively or additionally, the simulation unit for simulating the effect of a gaze of the second eye can be designed to take account of the orientation determined by the orientation sensor and/or the movement determined by the motion sensor and/or the inclination determined by the inclination sensor in the simulation of the effect of the gaze of the second eye of the user through the spectacle lens to be demonstrated for the second eye. To put it another way, the orientation, motion, and/or inclination sensors are intended to determine the instantaneous head position and/or the instantaneous movement of the head of the user and, on the basis of this information, to move the test images such that the visual impression for both eyes for the system eye-spectacle lens with the inclusion of the head movements determined by a so-called head tracker is demonstrated in the best possible way.

The first imaging optical unit and, if appropriate, the second imaging optical unit may be designed to be manually variable. In particular, a rotary adjustment mechanism operable by the user may be provided to displace the respective imaging optical unit or a lens of the respective imaging optical unit in a perpendicular direction with respect to the first image plane. A rotary adjustment mechanism operable by the user may also be provided to rotate or displace the respective imaging optical unit parallel to the first image plane. The respective displacement may also be realized by means of a slide operable by the user. The above-described tilting of the respective imaging optical unit or of a lens of the respective imaging optical unit in relation to the orientation of the holding device may also be embodied as a mechanically operable adjustment mechanism.

It may be advantageous for the adjustment mechanisms for the respective imaging optical units to be embodied such that they are automatically operable rather than manually operable. Such a variant therefore provides an automatic variation unit for varying the first imaging optical unit, which is secured to the holding device. Alternatively or additionally, an automatic variation unit for varying the second imaging optical unit may be provided, which is secured to the holding device. The operation may then be carried out, for example, via an input panel or an input knob or the like of the computer which generates the test image (with or without a simulation function of the effect of the gaze of an eye through a spectacle lens). It is also possible for provision to be made of an operating element e.g. in the form of a knob, small wheel, joystick or the like which drives the variation unit. The variation of the first and, if appropriate, of the second imaging optical unit that is performed by the automatic variation unit may be designed to operate under the influence of software. In particular, the first and, if appropriate, the second imaging optical unit may be designed to be focusable under the influence of software to thereby bring about an accommodation effort for the user.

It may also be advantageous to design one or both refraction determining optical units to be automatically operable. In particular, provision may be made for embodying the measuring spectacle lenses such that they are automatically exchangeable or replaceable. The toric or cylindrical measuring spectacle lenses may be embodied such that they are automatically rotatable. It is also possible for the apparatus that is used instead of the measuring spectacle lenses and including the lens having the different cylindrical zones and, if appropriate, the second lens having a spherical effect to be embodied such that it is automatically drivable.

Alternatively or additionally, a manual operating part may be provided, which is operated, for example, by a service provider who advises the user of the display device, and which is configured to vary the first and, if appropriate, the second imaging optical unit in accordance with the above description.

One particularly advantageous exemplary embodiment of a display device according to the invention comprising an automatic variation unit provides for the automatic variation unit for varying the first imaging optical unit to be designed to vary the first imaging optical unit on the basis of the orientation determined by the abovementioned orientation sensor and/or on the basis of the movement determined by the above-specified motion sensor and/or on the basis of the inclination determined by the above-described inclination sensor. Alternatively or additionally, the automatic variation unit for varying the second imaging optical unit may be designed to vary the second imaging optical unit on the basis of the orientation determined by the orientation sensor and/or on the basis of the movement determined by the motion sensor and/or on the basis of the inclination determined by the inclination sensor.

A further exemplary embodiment of the display device according to the invention relies on a first viewing direction determining unit to be mounted on the holding device to determine the direction of the gaze of the first eye. Alternatively or additionally, a second viewing direction determining unit may be provided on the holding device to determine the direction of the gaze of the second eye. The respective viewing directions determined may also influence the simulation calculation of the respective simulation units and/or the automatic variation of the respective imaging optical units that is performed by the variation unit. Gaze determining units known from the related art are so-called eye trackers that determine the pupil center and the pivot point of the eye and derive an instantaneous viewing direction therefrom.

In particular, the simulation unit for simulating the effect of a gaze of the first eye may be designed to take account of the direction of the gaze of the first eye, the direction being determined by the first viewing direction determining unit, in the simulation. Alternatively or additionally, the simulation unit for simulating the effect of a gaze of the second eye may be designed to take account of the direction of the gaze of the second eye, the direction being determined by the second viewing direction determining unit, in the simulation.

A further embodiment variant of the invention is wherein the automatic variation unit for varying the first imaging optical unit is designed to vary the first imaging optical unit on the basis of the direction of the gaze of the first eye, the direction being determined by the first viewing direction determining unit. Alternatively or additionally, the automatic variation unit for varying the second imaging optical unit may be designed to vary the second imaging optical unit on the basis of the direction of the gaze of the second eye, the direction being determined by the second viewing direction determining unit. A combination of these embodiment variants make it possible to determine the focusing state of the first and second imaging optical units from the respective viewing directions of both eyes.

In a further exemplary embodiment of a display device according to the invention, the holding device carries a first camera having an optical axis, the camera being controlled by the viewing direction of the first eye.

The optical axis is a term from geometric optics. The straight line that corresponds to the axis of symmetry of a reflective or refractive optical element or optical system is designated as optical axis. In a lens system, the optical axis is the line formed by the optical axes of the individual elements.

The first camera is controlled in such a way that the optical axis of the first camera and an optical axis running through the pupil center of the first eye in the viewing direction of the first eye correspond. The holding device carries a first distance sensor arranged in such a way that the first distance sensor detects a distance to an object recorded by the first camera in the form of a camera image. The simulation unit for simulating the effect of a gaze of the first eye of the user through a spectacle lens to be demonstrated for the first eye is configured to simulate the image generated by the first image generator in the first image plane from the camera image recorded by the first camera and from the distance detected by the first distance sensor. Alternatively or additionally, the holding device may carry a second camera having an optical axis, the camera being controlled by the viewing direction of the second eye in such a way that the optical axis of the second camera and an optical axis running in the viewing direction of the second eye through the pupil center of the second eye correspond. The holding device furthermore carries a second distance sensor arranged in such a way that the second distance sensor detects a distance to an object recorded by the second camera in the form of a camera image. The simulation unit for simulating the effect of a gaze of the second eye of the user through a spectacle lens to be demonstrated for the second eye is configured to simulate the image generated by the image generator in the first image plane and/or the image generated by the second image generator in the second image plane from the camera image recorded by the second camera and from the distance detected by the second distance sensor.

To put it another way, the invention provides, if appropriate respectively for each eye, a camera—preferably having a short focal length—with a viewing direction toward the front relative to the head position of the wearer, which allows the camera image thereby recorded to be altered computationally such that the image corresponds to the view through spectacles with the spectacle lenses to be demonstrated. In the case where two cameras are used, one for each eye, the cameras are preferably arranged at a customary eye distance from one another to realistically image the stereoscopic effect. In particular, their respectively recorded camera images are intended to be altered computationally such that each image corresponds to the view through the associated spectacle lens of the spectacles with the spectacle lenses to be demonstrated.

In one particular exemplary embodiment of the invention, provision is made for determining the distance of the point sighted by the user in the image plane by means of stereoscopic evaluation from the two camera images and for deflecting the focusing units of the imaging optical units such that the accommodation effort required for the sighted direction becomes necessary for the subject in order to accommodate the corresponding point in the on the test images taking account of the spectacle lens to be demonstrated.

The invention furthermore comprises a system having a display device of the type described above and a manual operating unit for automatically driving the first and, if appropriate, the second refraction determining optical unit and/or for automatically driving the first and, if appropriate, the second imaging optical unit and/or for driving the simulation unit(s).

The user of the display device may obtain the manual operating unit, for example, which acts on the display device by radio or electromagnetic signals, in order that the user passes feedback messages to the method. The feedback messages may be binary signals (e.g., pressing of knob). Scalar feedback messages may also be provided (e.g. rotary knob positions, joystick excursions, trackball positions).

The scalar feedback messages may be used, for example, to the effect that the user thereby acts on the focusable imaging optical unit(s) or on refraction determining optical unit(s), in particular the cylindrical or toric measuring spectacle lenses, to determine a subjective optimum.

With the aid of the manual operating unit, using software it may be possible to exchange the type of simulated spectacle lenses for a short period, such that the user may experience the use properties of different types in a comparison.

As an alternative to the user of the display device himself/herself, a service provider who advises the user in the selection of spectacles, by means of a manual operating unit acting electrically or by radio or a comparable method such as, for example, WLAN, Bluetooth or the like, may also influence the hardware and software components of the display device in order to select the use situations to be simulated in each case.

Instead of a display device comprising an image generator held by the holding device of the display device, the invention provides a system which contains a holding device which can be placed onto the head of a user, furthermore a first imaging optical unit secured to the holding device and designed to image an image generated by a first image generator in a first image plane such that the user can perceive the image with a first eye when the holding device is placed on the head, wherein the holding device carries a first refraction determining optical unit designed for determining the subjective refraction of the first eye when the holding device is placed on the head, and/or in that the first imaging optical unit is designed to be variable. In a departure from the display device described above, the image generator is not held by the holding device, but rather is arranged in a spatial area.

The further features described above in association with the configuration variants of the display device may advantageously also be realized in the embodiment variants of the system.

One particularly advantageous embodiment variant of the system consists in the fact that a second imaging optical unit designed to be variable is also secured to the holding device, the second imaging optical unit being designed to image the image generated in the first image plane such that the user can perceive the image with the second eye when the holding device is in the placed state, and/or in that the holding device carries a second refraction determining optical unit designed for determining the subjective refraction of the second eye when the holding device is in the placed state. In this variant, it is expedient if an image separating system is provided in order to feed first image contents of the image generated in the image plane exclusively to the first eye and second image contents, deviating from the first image contents, exclusively to the second eye.

In a further exemplary embodiment, a display device is provided that includes a holding device which can be placed onto the head of a user, a first image generator secured to the holding device and serving for generating an image in a first image plane (E) or a receptacle for receiving the first image generator in such a way that the first image plane (E), in which the image of the first image generator is generated, is arranged in a predetermined position in relation to the holding device, and a first imaging optical unit secured to the holding device and designed to image an image generated by the first image generator in a first image plane (E) such that the user can perceive the image with a first eye (LA) when the holding device is in the state placed on the head, wherein the holding device carries a first refraction determining optical unit designed for determining the subjective refraction of the first eye (LA) when the holding device is in the state placed on the head, and/or wherein the first imaging optical unit is designed to be variable.

In yet another exemplary embodiment, the display device contains a first imaging optical unit that is designed to be variable by virtue of the fact that the first imaging optical unit has at least one lens which is designed to be displaceable perpendicularly to the first image plane (E) and/or that the first imaging optical unit has at least one lens which is designed to be rotatable and/or displaceable parallel to the first image plane (E).

In an additional exemplary embodiment, the display device contains a first refraction determining optical unit including one exchangeable measuring spectacle lens or a first refraction determining optical unit including two measuring spectacle lenses that are rotatable relative to one another about a common optical axis or a the first refraction determining optical unit including two measuring spectacle lenses displaceable relative to one another in the form of Alvarez lenses; or a first refraction determining optical unit including a lens having a plurality of adjacent first zones arranged over the lens in a first direction, wherein each first zone has a different average power, wherein a plurality of adjacent second zones are arranged over the first lens in a second direction perpendicular to the first direction, wherein each second zone has a different cylinder power, wherein the first zones arranged over the first lens in the first direction overlap the second zones arranged over the first lens in the second direction, wherein the lens is designed to be rotatable and/or displaceable parallel to the first image plane (E).

In yet another exemplary embodiment, the display device includes a first image generator that is arranged in an exchangeable fashion in the first image plane (E).

In an additional exemplary embodiment, the display device contains a second imaging optical unit designed to be variable is secured to the holding device, the second imaging optical unit being designed to image the image generated in the first image plane (E) or an image generated by a second image generator in a second image plane such that the user can perceive the image with the second eye (RA) when the holding device is in the state placed on the head, and/or in that the holding device carries a second refraction determining optical unit designed for determining the subjective refraction of the second eye (RA) when the holding device is in the state placed on the head.

In yet another exemplary embodiment, the display device contains a first imaging optical unit and a second imaging optical unit that are designed complementarily to one another and/or the first refraction determining optical unit and the second refraction determining optical unit are designed complementarily to one another.

In an additional exemplary embodiment, the display device contains an orientation sensor for determining the orientation of the holding device, and/or a motion sensor for determining the movement of the holding device, and/or an inclination sensor for determining the inclination of the holding device, which are/is mounted on the holding device.

In yet another exemplary embodiment, the display device contains a simulation unit for simulating the effect of a gaze of the first eye (LA) of the user through a spectacle lens to be demonstrated for the first eye (LA) and for outputting the simulation of the effect of the gaze of the first eye (LA) of the user through the spectacle lens to be demonstrated for the first eye (LA) in the form of one image in the first image plane (E) by means of the first image generator and/or a simulation unit for simulating the effect of a gaze of the second eye (RA) of the user through a spectacle lens to be demonstrated for the right eye (RA) and for outputting the simulation of the effect of the gaze of the second eye (RA) of the user through the spectacle lens to be demonstrated for the second eye (RA) in the form of one image in the first image plane (E) by means of the first image generator or in the form of one image in the second image plane by means of the second image generator.

In an additional exemplary embodiment, the display device includes a simulation unit for simulating the effect of a gaze of the first eye (LA) that is designed to take account of the orientation determined by the orientation sensor, and/or the movement determined by the motion sensor, and/or the inclination determined by the inclination sensor in the simulation of the effect of the gaze of the first eye (LA) of the user through the spectacle lens to be demonstrated for the first eye (LA), and/or a simulation unit for simulating the effect of a gaze of the second eye (RA) that is designed to take account of the orientation determined by the orientation sensor and/or the movement determined by the motion sensor, and/or the inclination determined by the inclination sensor in the simulation of the effect of the gaze of the second eye (RA) of the user through the spectacle lens to be demonstrated for the second eye (RA).

In yet another exemplary embodiment, the display device contains an automatic variation unit for varying the first imaging optical unit that is secured to the holding device, and/or an automatic variation unit for varying the second imaging optical unit that is secured to the holding device.

In an additional exemplary embodiment, the display device contains an automatic variation unit for varying the first imaging optical unit that is designed to vary the first imaging optical unit on the basis of the orientation determined by the orientation sensor, and/or on the basis of the movement determined by the motion sensor, and/or on the basis of the inclination determined by the inclination sensor, and/or an automatic variation unit for varying the second imaging optical unit that is designed to vary the second imaging optical unit on the basis of the orientation determined by the orientation sensor, and/or on the basis of the movement determined by the motion sensor, and/or on the basis of the inclination determined by the inclination sensor.

In yet another exemplary embodiment, the display device contains a first viewing direction determining unit that is provided on the holding device to determine the direction of the gaze of the first eye (LA), and/or a second viewing direction determining unit that is provided on the holding device to determine the direction of the gaze of the second eye (RA).

In an additional exemplary embodiment, the display device contains a simulation unit for simulating the effect of a gaze of the first eye (LA) that is designed to take account of the direction of the gaze of the first eye (LA), the direction being determined by the first viewing direction determining unit in the simulation, and/or a simulation unit for simulating the effect of a gaze of the second eye (RA) that is designed to take account of the direction of the gaze of the second eye (RA), the direction being determined by the second viewing direction determining unit in the simulation.

In yet another exemplary embodiment, the display device includes an automatic variation unit for varying the first imaging optical unit that is designed to vary the first imaging optical unit on the basis of the direction of the gaze of the first eye (LA), the direction being determined by the first viewing direction determining unit, and/or an automatic variation unit for varying the second imaging optical unit that is designed to vary the second imaging optical unit on the basis of the direction of the gaze of the second eye (RA), the direction being determined by the second viewing direction determining unit.

In an additional exemplary embodiment, the display device contains a holding device that carries a first camera having an optical axis, the camera being controlled by the viewing direction of the first eye in such a way that the optical axis of the first camera and an optical axis running in the viewing direction of the first eye (LA) through the pupil center of the first eye (LA) correspond, and a holding device that carries a first distance sensor arranged in such a way that the first distance sensor detects a distance to an object recorded by the first camera in the form of a camera image, and in that the simulation unit for simulating the effect of a gaze of the first eye (LA) of the user through a spectacle lens to be demonstrated for the first eye (LA) is configured to simulate the image generated by the first image generator in the first image plane (E) from the camera image recorded by the first camera and from the distance detected by the first distance sensor, and/or a holding device that carries a second camera having an optical axis, the camera being controlled by the viewing direction of the second eye (RA) in such a way that the optical axis of the second camera and an optical axis running in the viewing direction of the second eye through the pupil center of the second eye (RA) correspond, and the holding device carrying a second distance sensor arranged in such a way that the second distance sensor detects a distance to an object recorded by the second camera in the form of a camera image, and in that the simulation unit for simulating the effect of a gaze of the second eye (RA) of the user through a spectacle lens to be demonstrated for the second eye (RA) is configured to simulate the image generated by the image generator in the first image plane (E) and/or the image generated by the second image generator in the second image plane (E') from the camera image recorded by the second camera and from the distance detected by the second distance sensor.

In yet another exemplary embodiment, a system includes a display device and a manual operating unit for driving the first refraction determining optical unit and/or the first imaging optical unit and/or the simulation unit.

In an additional exemplary embodiment, a system includes a first image generator and a holding device which can be placed onto the head of a user, comprising a first imaging optical unit secured to the holding device and designed to image an image generated by the first image generator in a first image plane (E) such that the user can perceive the image with a first eye (LA) when the holding device is in the state placed on the head, wherein the holding device carries a first refraction determining optical unit designed for determining the subjective refraction of the first eye (LA) when the holding device is in the state placed on the head, and/or in that the first imaging optical unit is designed to be variable.

In yet another exemplary embodiment, the system includes a second imaging optical unit designed to be variable that is secured to the holding device, the second imaging optical unit being designed to image the image generated in the first image plane such that the user can perceive the image with the second eye (RA) when the holding device is in the state placed on the head, and/or in that the holding device carries a second refraction determining optical unit designed for determining the subjective refraction of the second eye (RA) when the holding device is in the state placed on the head, and in that an image separating system is provided in order to feed first image contents of the image generated in the image plane (E) exclusively to the first eye (LA) and second image contents, deviating from the first image contents, exclusively to the second eye (RA).

BRIEF DESCRIPTION OF THE DRAWINGS

The invention will now be described with reference to the drawings wherein.

DESCRIPTION OF EXEMPLARY EMBODIMENTS

Figure 1:
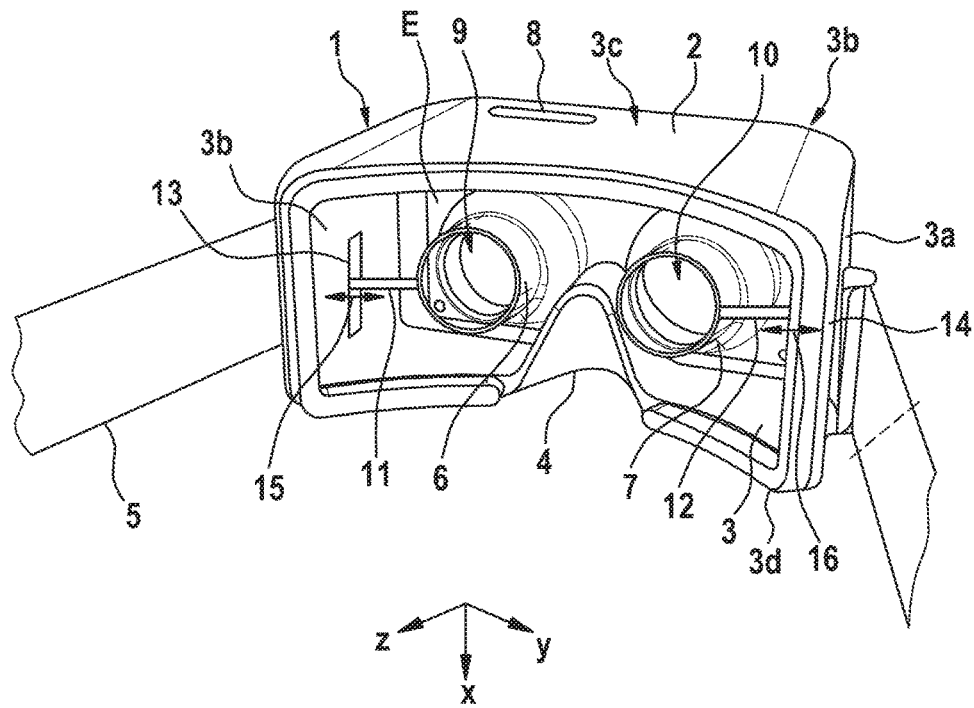
FIG. 1 shows a perspective illustration of a first exemplary embodiment of the display device according to the invention.

FIG. 1 shows a first exemplary embodiment of the display device 1 according to the invention schematically in a perspective illustration. The display device 1 comprises a front part 2 having an open side 3, the front part being designed substantially in a box-shaped fashion. All other sides 3a, 3b, 3c, 3d, 3e of the front part 2 are at least substantially closed. The contour of the open side 3 is designed such that it can be placed onto the head of a user such that the user can wear the display device 1 on the head like spectacles. For this purpose, the contour has a nose rest 4 and a holding band 5 is secured to the two lateral ends of the front part 2. The holding band 5 is led around the user's head when wearing the display device 1 according to the invention, such that the desired contact pressure is present to be able to wear the display device 1 ergonomically and preferably in a light-tight fashion on the head. The holding band 5 may be designed, for example, as an elastic band and/or as a band having an adjustable length. The front part 2 together with the holding band 5 forms a holding device which can be placed onto the head of the user.

The display device 1 according to an exemplary embodiment of the invention includes a first imaging optical unit 6 having an optical axis OA6 for a left eye LA of the user and a second imaging optical unit 7 having an optical axis OA7 for a right eye RA of the user, which respectively image an image generated in an image plane E in a manner magnified such that the user can perceive the image. This can best be seen in FIG. 2, which shows a schematic horizontal cross section of the display device 1 according to an exemplary embodiment of the invention.

Besides the imaging optical units 6 and 7, the display device 1 according to an exemplary embodiment of the invention has a first refraction determining optical unit 9 in the form of a measuring spectacle lens, the refraction determining optical unit being configured to determine the subjective refraction of the left eye LA when the holding device 2 is placed on the head of the user. Furthermore, provision is made of a second refraction determining optical unit 10 for determining the subjective refraction of the right eye RA, the second refraction determining optical unit being designed as a measuring spectacle lens. The measuring spectacle lenses 9 and 10 are exchangeable by means of corresponding holders 11 and 12 via openings 13 and 14 in the front part 2, which is clarified by the two double-headed arrows 15 and 16 in FIGS. 1 and 2.

The front part 2 is designed such that it is substantially closed apart from the side 3. In one exemplary embodiment, these sides 3a, 3b, 3c, 3d, and 3e are completely closed apart from the openings 13 and 14, which brings about a compartmentalization of light from outside. In another exemplary embodiment, which can be gathered from FIG. 1, ventilation slots 8 and/or ventilation holes are additionally introduced in sides 3a, 3b, 3c, 3d, and 3e, and are particularly preferably designed such that the light passing through them from outside is minimized.

Since the front part 2 is designed such that it is substantially closed apart from the side 3, the user, when wearing the display device 1 as intended on the head, can only perceive the images generated in the image plane E and can no longer perceive the surroundings.

Figure 2:
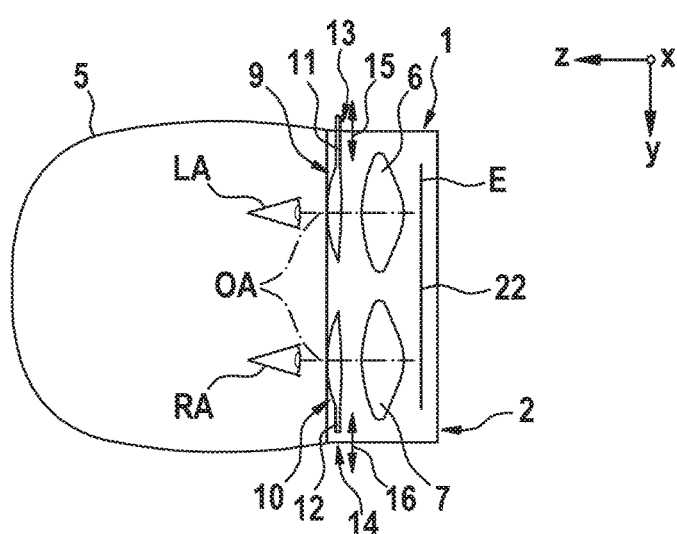
FIG. 2 shows a plan view of the exemplary embodiment of FIG. 1.
Figure 3:
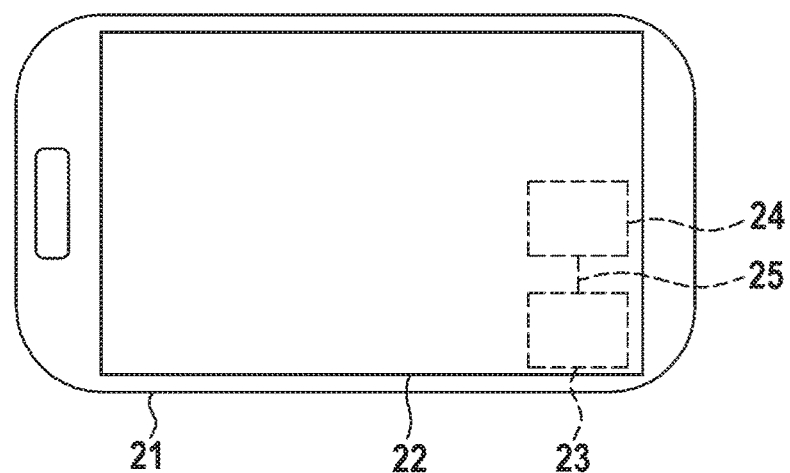
FIG. 3 shows a plan view of the image generator arranged in the display device 1.

For image generation, the display device 1 according to an exemplary embodiment of the invention may have a portable image generator in the form of a smartphone 21—illustrated by way of example in FIG. 3—having a screen 22, which is arranged in the display device 1 such that the screen 22 of the portable image generator 21 lies in the image plane E. Only the screen 22 is depicted schematically in FIG. 2 to simplify the illustration, and only the image plane E, rather than the entire image generator 21 is illustrated in FIG. 1, to simplify the illustration.

For the purpose of rapidly exchanging the image generator 1, a holder is provided, including a frame having a frame base (not shown). A cutout is provided in the frame base, the cutout being situated opposite a rear-side camera of the portable image generator 21. The frame can be inserted laterally into a receptacle provided in the front part 2. Two resilience elements are present in the receptacle and engage in a latching fashion on a latch of the frame in such a way that when the frame is inserted into the receptacle, the correct seating of the frame in the receptacle is mediated and the frame is fixed in an exchangeable fashion in this position. Alternatively, for this purpose, in each case two small permanent magnets or magnetizable small metal disks are provided in the receptacle at the top side and underside and also at the positions of the frame corresponding thereto. The front areal termination of the front part 2 is formed by a partly transparent plastic disk. The disk is coated in a partly reflective fashion, such that the image generator 21 used is not discernible or is hardly discernible from outside, but a rear-side camera of the image generator 21 can look toward the outside.

The smartphone 21 illustrated by way of example in FIG. 3 has a screen 22, acting as an image generator, a control unit 23, and also a sensor unit 24 for detecting a movement of the smartphone 21, the sensor unit being connected to the control unit 23 via a control line 25. Further elements required for the operation of the smartphone 21 are not shown. The control unit 23 and the sensor unit 24 are illustrated in a dashed fashion since they are installed in the smartphone 21 and are normally not visible from outside.

The control unit 23 can execute program instructions and serves for driving the screen 22.

The sensor unit 24 may have an inertial sensor, such as, for example, a 1-axis, 2-axis or 3-15 axis gyroscope, an inclination sensor, an acceleration sensor, and/or any other sensor which makes it possible to detect a movement of the smartphone 21. The sensor unit 24 generates corresponding measurement signals, which are transmitted (preferably continuously) to the control unit 23, as illustrated schematically by the dashed connecting line 25 in FIG. 3.

Figure 4:
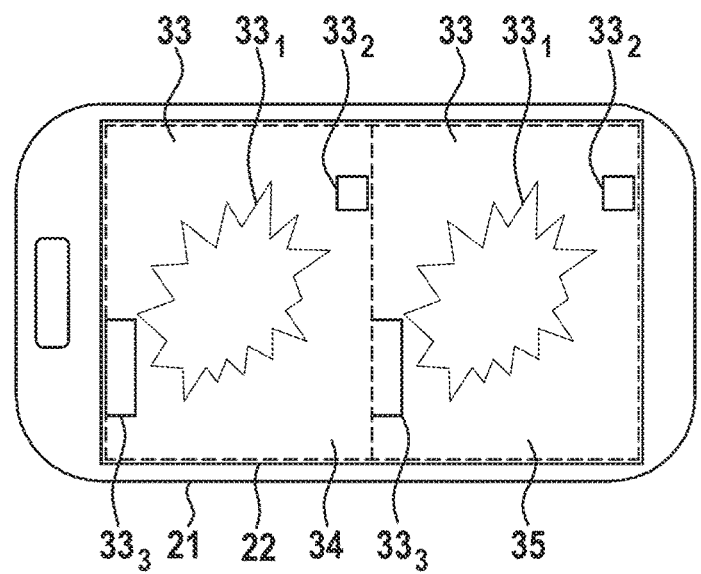
FIG. 4 shows a plan view of the image generator in accordance with FIG. 3 for elucidating the division of the screen into two sections and the representation of the same images in both sections.

As is evident from FIG. 2, each of the two imaging optical units 6 and 7 images only a partial region of the screen 22. For a user wearing the display device 1 on the head to perceive an object to be represented with both eyes LA, RA, the object has to be generated in the associated partial regions of the screen 22, which are imaged by the two imaging optical units 6 and 7. For this purpose, provision is made of an application or a program on the smartphone 21 which is executed by the control unit 23 and drives the screen 22 such that on the basis of supplied image data for the object to be represented or for a first image to be represented, the object or the first image 33 is generated with schematically represented image elements $33_1$, $33_2$ and $33_3$ both on a first section 34 of the screen 22 and on a second section 35 of the screen, the second section being separate from the first section 34, as is shown in FIG. 4.

Since the application is executed on the smartphone 21 itself, image data stored on the smartphone 21 or image data supplied to the smartphone 21 (e.g., streamed image data, preferably via a suitable wireless connection) can advantageously be used to generate the representation of the images in the two sections 34 and 35. In particular, image data originating from other applications running on the smartphone 21 can be conditioned by the application according to the invention such that the same image is always represented in both sections 34 and 35.

The two sections 34 and 35 can be chosen such that they directly adjoin one another. Alternatively, it is possible for the sections to be spaced apart from one another. The spacing region can be represented or driven in particular as a blanked region. The application can represent the images 33 in the two sections 34, 35 such that no stereo effect is present for the user. However, it is also possible to generate a stereo effect. The basic construction of the overall system of display device 1 comprising the screen 22 divided into the sections 34 and 35, the two imaging optical units 6 and 7, the exchangeable measuring spectacle lenses $9_1$, $9_2$, $10_1$, and $10_2$, and stereo image observer 17 can be gathered from FIG. 5.

Further functionalities of the smartphone 21 and/or of the display device 1, in particular the operating control thereof, are described in DE 10 2014 107 938 A1 and in DE 10 2014 017 534 A1.

The measuring spectacle lenses $9_1$, $9_2$, $10_1$, and $10_2$ are constructed similarly to those of the precision measuring spectacles from ZEISS®. The task of the measuring spectacle lenses 9 and 10 is to adapt the stereo image observer 17 for the smartphone screen 22, such that the user can see sharply image points that are apparently at infinity, that is to say that the user's refraction deficit (expressed, e.g., in sphere, cylinder, and axis thereof) is thereby compensated for. The measuring spectacle lenses $9_1$, $9_2$, $10_1$, and $10_2$ are spherical, toric or cylindrical single-vision lenses having a relatively small diameter which are arranged relatively close to the eye LA, RA and, therefore, nevertheless ensure a sufficiently large field of view. The measuring spectacle lenses $9_1$, $9_2$, $10_1$, and $10_2$ are used to demonstrate to the user 17 the correction of his/her new spectacles. Alternatively or supplementarily, the spherical portion can also be brought about by a targeted defocusing of the imaging optical units of the stereo image observer by a change of position in the direction of the optical axis thereof.

With the aid of software running on the smartphone 21 itself and/or an additional part of the software, the additional part running on a computer (not illustrated) connected to the smartphone 21 by wire, optical waveguide or radio technology, scenes are presented to the user 17 according to the invention. In this case, the software also accesses the position and orientation sensors 24 of the smartphone 21, such that a head movement of the user 17 leads to a variation of the image segments 34 and 35 shown, which are calculated such that the image impression with spectacle lenses to be demonstrated is simulated for the user 17. In particular, the two images 34 and 35 are calculated such that they produce a stereoscopic impression of the scene to be represented.

The scene to be represented may be a scene measured in reality, but it may also be a purely calculated scene. Expediently, the scene has a depth extent. Part of the simulated representation may also be the rim of the spectacle frame. Even the user 17 himself/herself together with a spectacle frame to be demonstrated could be represented as a constituent part in the scene to be demonstrated.

The partial images 34 and 35 to be represented on the screen 21 are always calculated such that they take account of the head posture of the user 17 in the simulated scene. A movement of the head may entail a movement of the represented scene as though the user 17 were himself/herself in the scene at the point imagined. In particular, if the spectacle lens to be demonstrated is a multifocal lens, the view through the multifocal lens is also simulated. The visual impressions when gazing through various kinds of multifocal lenses can be presented to the user 17: bi- and trifocal lenses, various progressive lens designs, e.g., progression zones of different lengths, progressive lens types.

In the calculation, the blur as a result of astigmatic secondary effects of the spectacle lens, which is dependent on the respective passage point of the visual lines through the respective spectacle lens, is simulated by blur in the simulated scene.

Figure 5:
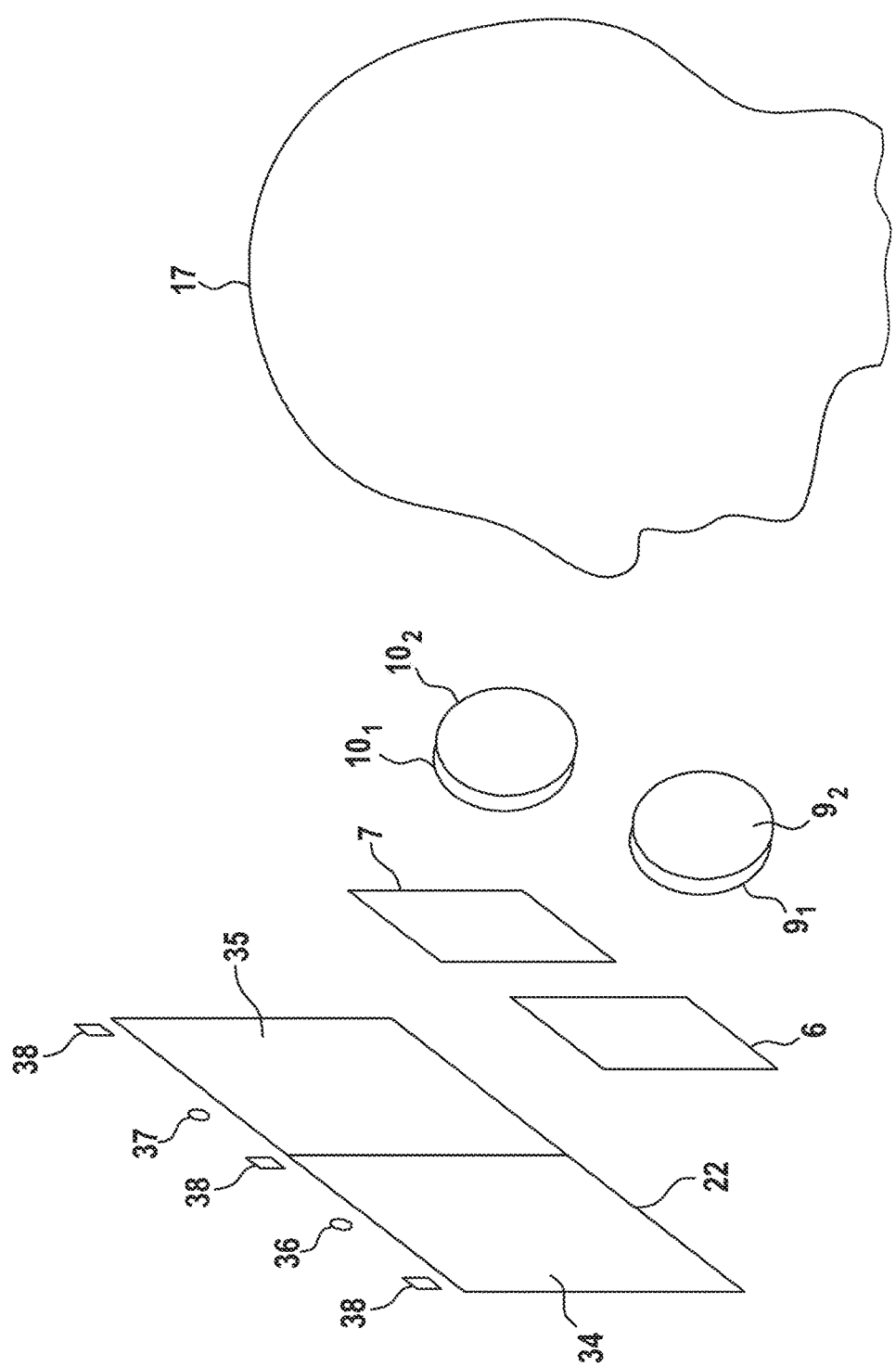
FIG. 5 shows a schematic illustration of an exemplary embodiment of the overall system according to the invention including a display device in the first exemplary embodiment according to FIG. 1—with the screen divided into sections, imaging optical units and exchangeable measuring spectacle lenses—and user.

The display device 1 may have one or a plurality of units with which the viewing directions of the two eyes LA, RA of the user can be determined individually. In the simplest case, as shown in FIG. 5, the units may be cameras 36 and 37, which are sensitive in the IR, at least one of which per eye LA and RA is directed at the associated eye LA and RA. In addition, an IR illumination 38 should advantageously be provided, which illuminates the space around the eyes LA and RA in the infrared. This illumination 38 is invisible to the user 17 and does not disturb the latter. It serves to enable the units 36 and 37 to determine the positions of the eyeballs (so-called eye tracker).

The two simulated partial images 34 and 35 are calculated separately in each case taking account of the detected viewing angles of both eyes LA and RA in the manner in which the respective impression would arise for an eye LA and RA looking in this direction, wherein for each line of sight in the case of the eye positions determined the prismatic effects such as would also occur upon viewing with corresponding eye positions become active in the representation. In this first variant, moreover, the blur that would arise as a result of erroneous spherical and astigmatic power for the respective visual lines is represented by local smearing (e.g., as convolution). To make the whole calculable more rapidly, it is possible here to make simplifications that do not adversely affect the demonstration purposes.

By wire, optical waveguide or radio, the display device 1 may likewise be connected to a screen (not illustrated here) that is seen by the optician or service providers providing assistance in the selection of spectacle lenses. By way of example, the represented scene of the user 17 can be imaged on the screen, the points in the scene which the user is currently fixating additionally being marked. These positions are determined by means of the signals of the units 36 and 37. The optician or service provider in a conversation with the user 17 can thus draw the user's attention in a targeted manner to one or another detail of the represented scene.

An alternative to cameras 36 and 37 that measure the positions of both eyeballs is based on the fact that in the interior of the display device 1 light beams that are invisible to the user 17 are directed at the eyeballs and the reflexes thereof are evaluated. The eyeball positions determined influence the calculation of the viewing directions and of the scene details to be shown for the viewing directions: They are, in particular: the prismatic deflection as a result of the respective visual line and the blur as a result of the astigmatism.

In association with a head movement and a simultaneous eye movement that compensates for the head movement, the prismatic deflections have the effect that lines that are straight in reality appear to be dynamically curved to the wearer of spectacles with progressive lenses (so-called "rocking effect"). The magnitude and exact type depend on the spectacle lens power, in particular on the addition and the progression length of a multifocal lens. As the wearing duration increases, the user becomes accustomed to this and the effect is perceived to a lesser extent or no longer perceived. The speed of adaptation of the user is manifested on an individual basis and, with the display device according to an exemplary embodiment of the invention, an optician or service provider who uses the display device for demonstrating spectacle lenses can determine whether a user will probably tolerate a specific type of progressive lens.

By means of an additional operating device (not illustrated), in particular a handheld device, such as e.g., a smartphone or a tablet, which is likewise connected to the smartphone 21 or to the abovementioned computer by wire, optical waveguide or radio technology, the optician can abruptly exchange, as it were, the spectacle lens to be simulated.

With the display device 1 according to an exemplary embodiment to the invention, in the case of progressive lenses for lateral viewing directions, in particular in the lower and there especially in the outer region, it is possible to check the compatibility of the computation of vertical prismatic secondary effects. These secondary effects are perceived in a disturbing manner to different extents individually. The demonstrating optician or service provider shows the user 17 very different designs and asks the user how he/she gets on with the visual impression in the scene chosen.

By pressing a knob, the optician or service provider can also exchange the scene, e.g., from a scene in a closed room to a scene outdoors in broad daylight, in a stairwell or in an automobile. In this way, the user can try out progressive-lens spectacles which physically do not exist at all, but which are adapted virtually to the user's refraction values.

Figure 6:
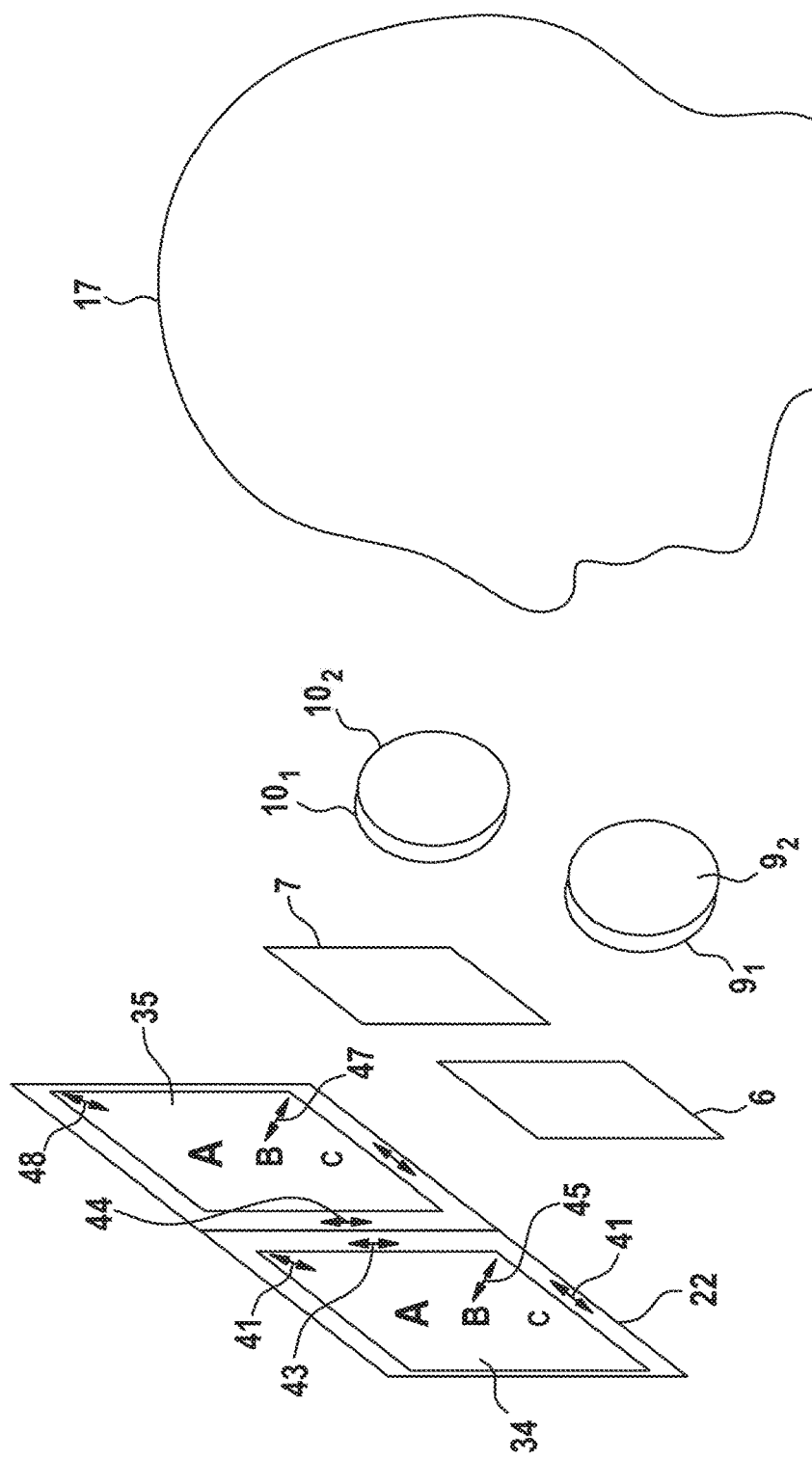
FIG. 6 shows the schematic illustration according to FIG. 5 supplemented by double-headed arrows for clarifying the displacement and scaling of the partial images displayed on the screen of the image generator for the right and left eyes.

Prismatic prescriptions can also be demonstrated with the means of the display device 1 described in the first exemplary embodiment. To that end, the two partial images 34 and 35 have to be displaced relative to one another by correctly calculated distances and directions, as is indicated by the double-headed arrows 41, 42, 43, and 44 shown in FIG. 6. For certain wearers 17 of spectacles, the images 34 and 35 of the right and left eyes RA and LA do not appear in the same size (aniseikonia). These users 17 have difficulties in fusing both images 34 and 35. This effect can be improved to a certain extent by suitable intrinsic magnification of the spectacle lenses. By means of software, it is possible to represent the right and left partial images 34, 35 with slightly different magnifications (cf. double-headed arrows 45, 46, 47, and 48) and thus to determine whether the user 17 will benefit from influencing the size of the two images 34 and 35 in a targeted manner in the real spectacles to be manufactured by means of the specific choice of the spectacle lenses, e.g., by means of different refractive indices of the spectacle lenses. Levels of anisometropia that are greater than 2 dpt. can lead to problems when the spectacles are worn, which problems can be alleviated with the aid of a "slab off" grinding. The optician can thus demonstrate to the user 17 the benefit of such a measure, without having available such a pair of spectacle lenses specifically with the refraction and use data of the user 17 and without fitting such lenses into a frame by grinding. Since, in the imaginary situation, the user 17 may be allowed to look into a mirror in the virtual scene, too, the user would be able to see via his/her appearance with the recommended spectacle frame and these spectacle lenses.

With the display device 1, it is possible to demonstrate to the user 17 the view through a polarizing spectacle lens in a virtual scene. Expediently, for this purpose a scene contains many approximately horizontal specularly reflective areas, the reflections of which are reduced by dint of software, e.g., wet roads with or without oncoming automobiles in sunshine or scenes on water.

The display device 1 can also be used to demonstrate to the user 17 the view through a phototropic spectacle lens in a virtual scene. Expediently, for this demonstration purpose a scene contains many different lighting conditions, e.g. representation in an automobile including travel through a tunnel, sitting in a café, etc.

The display device 1 can also be used to demonstrate to the user 17 virtual scenes with different lighting conditions. For this purpose, the user 17 expediently likewise obtains an operating device (not shown) which allows discrete or continuous variables to be set, e.g., the degree of darkening of sunglasses from e.g. 10% to 90% transmittance. For this purpose, the user may actuate for example a sliding controller or a joystick or a rotary knob. Discrete switching functions are used e.g. expediently for a fast change between different scenes or different demonstration objects.

With the aid of a visual mark in the virtual scene, which visual mark can be influenced by the user 17 via the latter's operating device (e.g., by means of a joystick or sliding controller, that is to say continuous operating elements), the unit according to an exemplary embodiment of the invention can be calibrated: during the calibration run, the user 17 thus influences for example the position of visual marks in the virtual scene, which the user brings subjectively to congruence there. These are visual marks which can also be shown against a single-colored background and which the user is intended to bring to congruence. From the position of the visual marks and the eye movements obtained by the units 36 and 37, the software calculates the position of the eye pivot point in the device coordinate system and the pupillary distance of the user (calibration).

Figure 7:
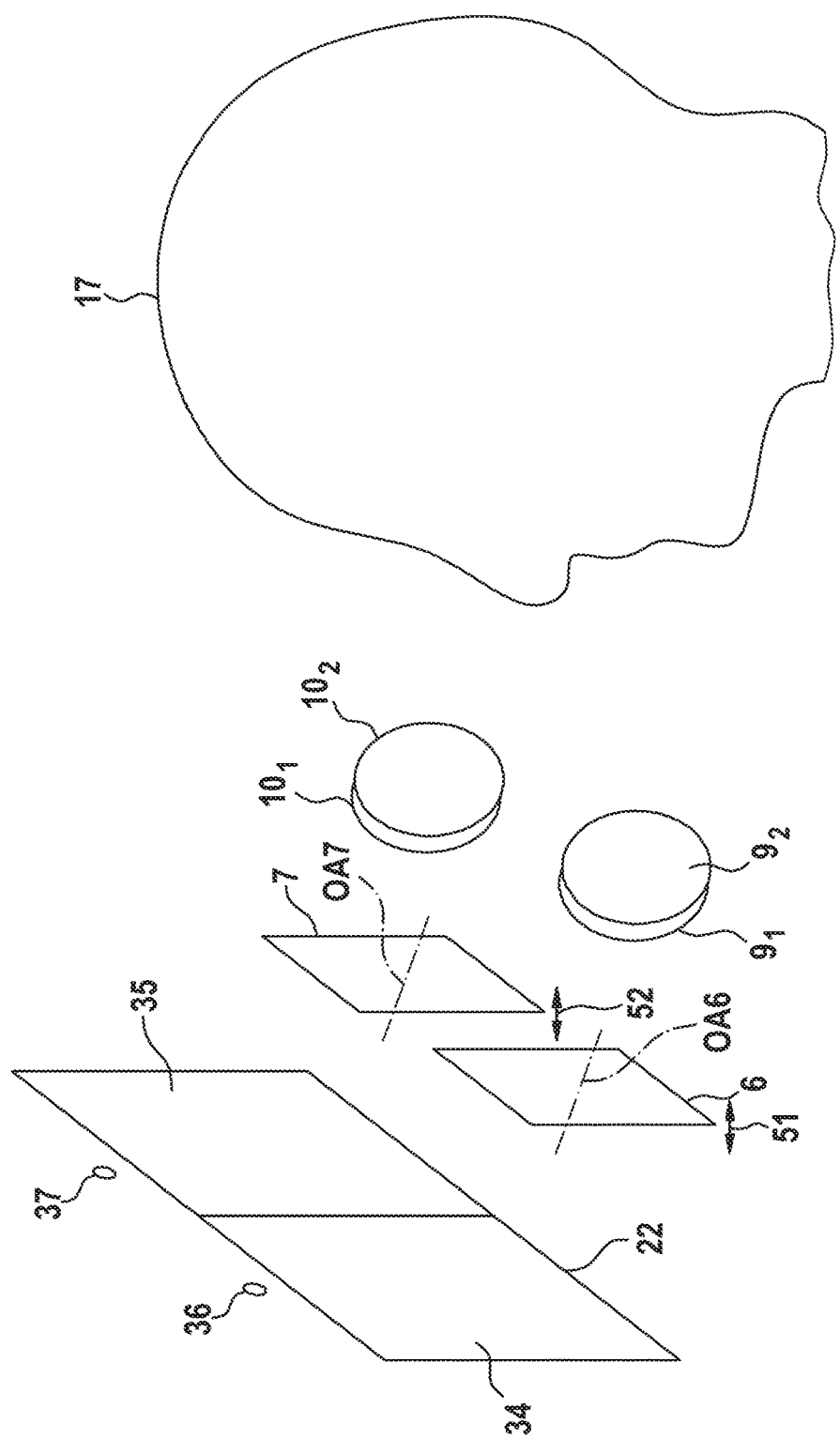
FIG. 7 shows a schematic illustration—corresponding to FIG. 5—of an overall system according to the invention having a display device in a second exemplary embodiment including a displaceable imaging optical units and a user.

FIG. 7 shows a schematic illustration—corresponding to FIG. 5—of an overall system according to an exemplary embodiment of the invention including a display device 1 in a second exemplary embodiment having variable imaging optical units 6 and 7 embodied in the form of displaceable focusable stereo magnifying lenses. The constituent parts of the overall system according to FIG. 7 correspond in principle to the constituent parts of the overall system according to FIGS. 5 and 6. Therefore, the same reference signs are applicable.

Figure 8:
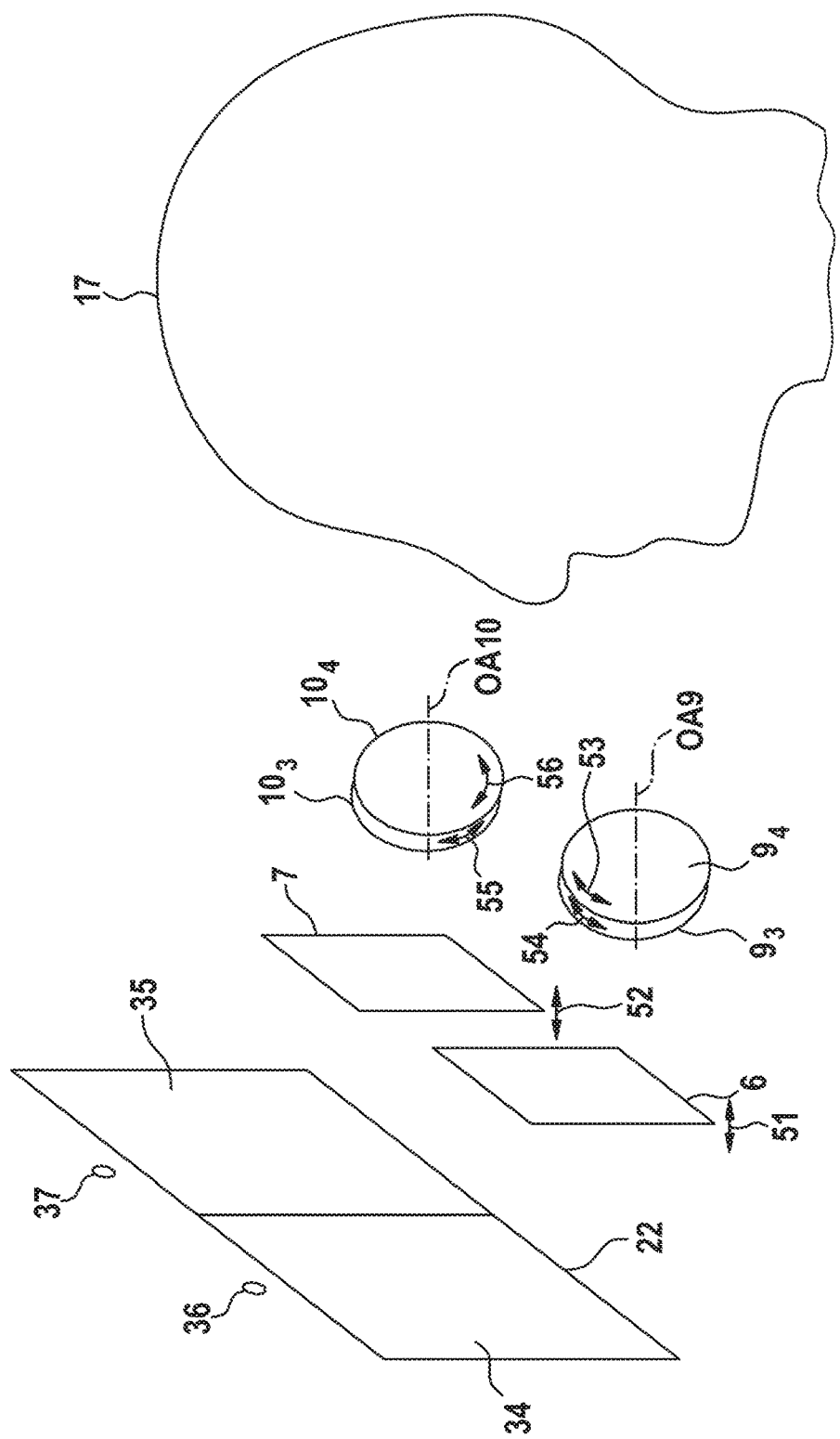
FIG. 8 shows a schematic illustration—corresponding to FIG. 5—of an overall system according to the invention including display device in a third exemplary embodiment having measuring spectacle lenses rotatable relative to one another and a user.

In this exemplary embodiment, the imaging optical units 6 and 7 of the stereo image observer 1 are arranged movably along their optical axes OA6 and OA7 under software control (FIG. 8, cf. direction arrows 51 and 52). As a result of this controlled movement, it is possible to bring about an accommodation stimulus for the user 17, such that the user 17 has to affect accommodation with his/her eyes LA and RA when gazing at points in the display 22 which lie nearer to the observer 17 in the represented space. The position of the lenses 6 and 7 is set respectively—depending on the viewing direction of the respective eye LA and RA—for each eye LA and RA independently of the other eye RA or LA, such that the user 17 himself/herself has to provide the full or a set portion of the accommodation effort required for the distance of the point fixated in the virtual scene, in the manner that the user 17 also has to affect accommodation in the case of progressive-lens spectacles depending on their addition and viewing direction and also the distance of the fixated detail.

A progressive lens does not always compensate for the entire accommodation effort of the wearer of spectacle lenses (user 17) by means of the near addition effect, but rather only a portion. Since the aberrations—particularly in the lateral regions—are greatly dependent on the addition and on the progression length of the spectacle lens, a progressive lens is provided only with the near addition that is actually required by the wearer of spectacle lenses for the vision habits and use habits of the wearer. The accommodation capability of the wearer of spectacle lenses is a factor governing whether the wearer can see sharply, in the distance regions of a represented scene, all objects situated there: if the accommodation capability of the wearer together with the addition power of the spectacle lens does not suffice, the wearer of spectacle lenses cannot see sharply at specific distances. The usability range toward the front or else toward the back is restricted e.g., by the combination of the spectacle lens with the accommodation capability of the wearer of spectacle lenses. If the accommodation capability of the wearer of spectacle lenses is completely compensated for by progressive-lens spectacles, however, for viewing directions in which customarily nearby objects are situated, despite a residual accommodation capability of e.g., 1 dpt, then the wearer of spectacle lenses is expected in addition to cope with unnecessarily high astigmatism, under certain circumstances, in the lateral regions. The prismatic effects become larger with increasing addition—in this case, especially the different vertical components between left and right eyes are disturbing. This test determines the reasonable near addition power for the user 17 by means of a realistic practical experiment, without this necessitating corresponding spectacles designed for the individual data of the user 17.

The electronically controlled focusing of the imaging optical units 6 and 7, which is introduced in the second exemplary embodiment and which depends dynamically on the viewing directions respectively chosen enables a simulation of the multifocal spectacles, in particular of progressive-lens spectacles, that goes significantly beyond the first exemplary embodiment. The benefit of the invention is that the effect of progressive-lens variants can be demonstrated very realistically and clearly.

Since the focusing of the imaging optical units 6 and 7 can concomitantly simulate part of the spherical prescription portion (which in the first exemplary embodiment is predefined exclusively by the measuring spectacle lenses $9_1$, $9_2$, $10_1$, and $10_2$), the correction of the spherical prescription portion can be shifted wholly or partly to the dynamic adjustability of the imaging optical units 6 and 7. That reduces the number of spherical measuring spectacle lenses to be kept available and it also facilitates the adaptation to the individual conditions of the individual user 17.

A third exemplary embodiment depicted schematically in FIG. 8 is based on the second exemplary embodiment depicted schematically in FIG. 7, and also replaces the cylindrical measuring spectacle lenses $9_1$ and $10_1$ according to FIG. 7 by in each case two toric or cylindrical lenses $9_3$, $9_4$, $10_3$, and $10_4$ that are electrically rotatable (cf. direction arrows 53, 54, 55, and 56) about a common axis OA9 and OA10 separately from one another. The combination of two such lenses $9_3$, $9_4$, $10_3$, and $10_4$ produces in the optical power a lens having adjustable astigmatic power. The magnitude of the cylinder power depends on the mutual rotation angle of these two lenses $9_3$, $9_4$, $10_3$, and $10_4$. Besides the cylindrical power, a resulting spherical portion also occurs as well. If both lenses have astigmatism of the same magnitude and they are mounted sufficiently close to one another, then the resulting cylindrical value may be assume to be double the magnitude of the individual lens $9_3$, $9_4$, $10_3$, and $10_4$ of this type. That is the case if the cylinder axes of both lenses $9_3$, $9_4$, $10_3$, and $10_4$ are parallel. The axis position of the resulting cylinder is then likewise the same.

By contrast, if the two cylinder axes are rotated by 90° relative to one another, then both lenses $9_3$, $9_4$, $10_3$, and $10_4$ together bring about only a spherical power. This power has to be taken into account in the driving (direction arrows 51 and 52) of the imaging optical units 6 and 7, such that the resulting spherical power of all these optical elements 6, 7, $9_3$, $9_4$, $10_3$, and $10_4$ is such as is precisely necessary for the simulation.

All other mutual rotation positions give rise to both a spherical and a cylindrical portion having a value of between the cylinder value and double the cylinder value of the individual lens $9_3$, $9_4$, $10_3$, and $10_4$. The resulting axis is the angle bisector between the axes of the cylinder lenses. If the appropriate mutual rotation angle has been set for both lenses $9_3$, $9_4$, $10_3$, and $10_4$, it is possible, by virtue of the fact that both lenses $9_3$, $9_4$, $10_3$, and $10_4$ are rotated jointly by the same angle, to set them such that the axis position of the resulting cylinder is that which would be desired to be set.

The electronic control of the position of the imaging optical units 6 and, 7 and of the lenses $9_3$, $9_4$, $10_3$, and $10_4$ then takes place under software control such that for the detected viewing direction exactly the spherical and astigmatic power arises which the spectacle lens to be demonstrated has there. The exact driving takes place in this case such that it also concomitantly takes account of the imperfections of the stereo observer magnifying lenses 6 and 7 for this viewing direction, such that the observer 17 obtains for the respectively fixated points exactly the optical stimuli which the observer would also experience with real spectacles (spherical, cylindrical incl. axial, prismatic powers).

In this case, the representation of the virtual scenes is simpler since the blur as a result of the astigmatism of oblique viewing directions (in the case of strong single-vision lenses or greatly curved sports spectacle lenses), as a result of the residual astigmatisms when gazing through a progressive lens to the right and left of the near region, etc. then arises automatically for the user 17 through the optical system 6, 7, $9_3$, $9_4$, $10_3$, and $10_4$ of the display device 1.

Instead of two spectacle lenses rotatable relative to one another, it is also possible to use two Alvarez lenses displaceable relative to one another in two coordinates, with which Alvarez lenses it is also possible to set any astigmatism/axis combination in a certain design range.

The adjustment mechanism comprising rotatable toric or cylindrical lenses or comprising lenses displaceable relative to one another is known from phoropters. What is novel is that these means are adjusted here dynamically depending on the viewing directions of both eyes, specifically such that they simulate in each case the effect of spectacles to be demonstrated.

Unlike in the previous example, in this case there is also no need for that part of the blur which arises as a result of the viewing-direction-dependent spherical mismatch to be calculated and represented in the scene images for the two eyes separately: if the position of all the optical components 6, 7, $9_3$, $9_4$, $10_3$, and $10_4$ is exactly like the spherical mismatch of the spectacle lens to be simulated, then the user 17 also experiences the same.

The astigmatic mismatch for the central visual line of the eyes LA and RA can also be calculated and set by means of targeted (de)focusing (imaging optical unit 6, 7) and the positions of the cylindrical lenses $9_3$, $9_4$, $10_3$, and $10_4$ in each case from the data of the spectacle lenses to be simulated and the eyeball positions: for the "central line" (along OA9 and OA10), the user 17 sees what he/she would also see with the spectacle lens (spherical and astigmatic errors, coma, etc. cannot be simulated in this way, however).

With a display device 1 configured in this way, an optician or service provider can demonstrate all aspects of different progressive lenses to a user 17. The optician or service provider can insert for the user, via the latter's operating part, marks which the user 17 should fixate, and request the user to compare his/her impression there with that of a different spectacle lens realization. The control programs of the display device 1 can also play back a task program for the user 17, measure the time until the user 17 provides feedback messages via the user's operating part and thus determine an objectified measure of the performance capability of the user 17 with in each case a plurality of progressive-lens variants.

In this way, the selection of progressive lenses that are subjectively less suitable is avoided because the display device 1 makes it possible to go through a plurality of spectacle lens supply variants with different parameters, without actually manufacturing all these solutions. That has not been done hitherto owing to the high costs, and the quality of a spectacle lens supply lacks the inventive display device 1. The result depends on many random factors, including very greatly on the level of verbal communication between the dispensing optician and the user 17.

With the solution according to the invention, however, the user 17 can also be allowed to exert an influence on parameters, e.g., on the optimum axis of a cylindrical prescription portion, by a procedure in which the user, by means of the latter's operating part, sets the subjectively optimum axis and subsequently, in an objective playful test step in which the user 17 has to fulfil specific visual tasks, checks on the basis of the reaction times of the user whether the latter actually has sharp vision.

Figure 9:
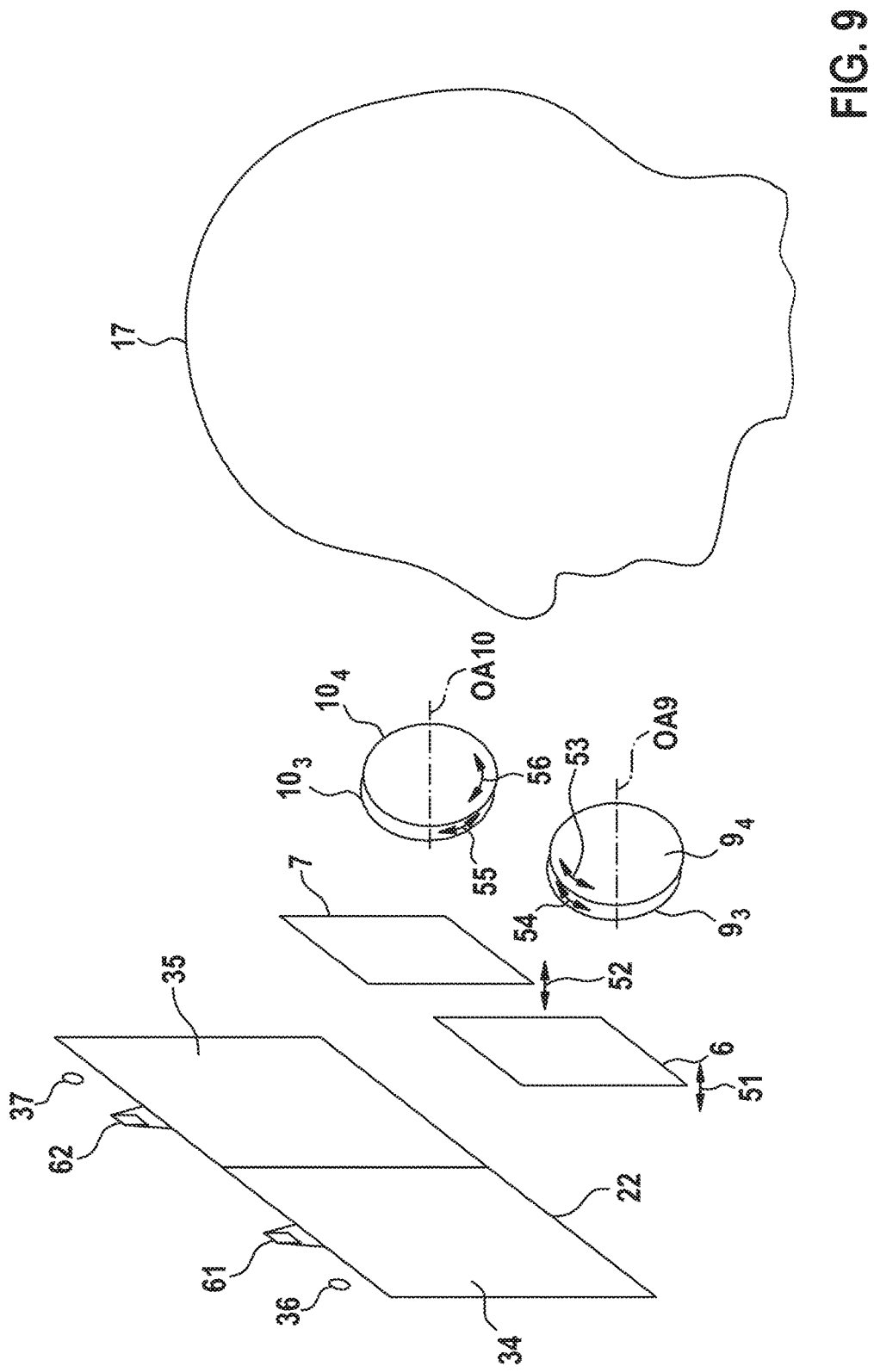
FIG. 9 shows a schematic illustration—corresponding to FIG. 5—of an overall system according to the invention including a display device in a fourth exemplary embodiment having additional front cameras and a user.

A fourth exemplary embodiment depicted schematically in FIG. 9 is based on the third exemplary embodiment and contains one or a plurality of additional front cameras 61 and 62 which look toward the front from the display device 1. The images of the front cameras 61, 62 are fed to a computer, which calculates the distances of associated points from the views. In this regard, the scene represented by the display device 1 may also become the real scene around the user 17 himself/herself by a procedure in which stereoscopic views are calculated from the calculated images 34, 35 with their depth gradation, the stereoscopic views being distorted in a manner as seen for the real scene upon viewing with the spectacle lens to be demonstrated.

With this exemplary embodiment, the demonstrating optician could give the user 17 a reading extract, for example. By means of the cameras 61, 62 and the unit (7, 7') for determining the eyeball positions, it is then possible to measure objectively at what viewing distances the user 17 holds the reading extract. The optician may ask the user to read out the reading extract, measure the user's reading speed, determine the viewing saccades, etc. In the case of the real reading extract, it is possible e.g. computationally to magnify or reduce, etc. the sample reading text in stages and thus to optimize the adaptation of the spectacles for vision tasks in the user-specific use situations by selection of differently devised progressive lens designs.

Instead of the screen moved concomitantly with the subject's head, it is also possible to take a spatially fixed projection area which allows the right and left images to be presented separately from one another, e.g., a 3D television screen. The device which has to be moved with the user's head becomes lighter and smaller as a result.

Upstream of the two imaging optical units 6, 7, the elements for image separation are then respectively fitted in order that the left eye sees only the calculated scene intended for the left eye, and the right eye that scene intended for the right eye, e.g., a diaphragm which alternately releases a view for the left image and the right image.

In front of the user's eye, moreover, there may be situated the above-described viewing direction sensors with which the system determines the viewing directions of the individual pupils, and the electronically driven optical components which, on the one hand, compensate for the individual refraction data and, on the other hand, by means of targeted focusing, initiate accommodation stimuli such as the wearer of spectacles would also have to apply in the virtually represented scene as the wearer of the spectacle lens to be demonstrated, in order to see sharply the details fixated in each case.

The foregoing description of the exemplary embodiments of the invention illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A display device comprising:
   a holding device that can be placed onto the head of a user;
      a first image generator secured to the holding device and configured to generate an image in a first image plane (E), or
      a receptacle for receiving the first image generator such that the first image plane (E), in which the image of the first image generator is generated, is arranged in a predetermined position in relation to the holding device; and
   a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user;
   wherein the holding device carries a first refraction determining optical unit configured to determine a subjective refraction of the first eye (LA) when the holding device is placed on the head of the user,
   wherein the first refraction determining optical unit has two measuring spectacle lenses displaceable relative to one another in the form of Alvarez lenses, or
   wherein the first refraction determining optical unit includes a lens having a plurality of adjacent first zones arranged over the lens in a first direction, wherein each first zone has a different average power, where a plurality of adjacent second zones is arranged over the first lens in a second direction perpendicular to the first direction, wherein each second zone has a different cylinder power, wherein the first zones arranged over the first lens in the first direction overlap the second zones arranged over the first lens in the second direction, and wherein the lens is configured to be rotatable, displaceable, or rotatable and displaceable parallel to the first image plane (E), and
   wherein the first imaging optical unit is arranged between the first image plane (E) and the first refraction determining optical unit.

2. The display device as claimed in claim 1, wherein the first imaging optical unit is configured to be variable.

3. The display device as claimed in claim 1, wherein the first imaging optical unit further includes at least one lens that is configured to be at least one of:
   displaceable perpendicularly to the first image plane (E), or
   displaceable parallel to the first image plane (E), or
   rotatable parallel to the first image plane (E).

4. The display device as claimed in claim 1, wherein the first image generator is arranged exchangeably in the first image plane (E).

5. The display device as claimed in claim 1, wherein a second imaging optical unit configured to be variable is secured to the holding device, the second imaging optical unit being configured to image the image generated in the first image plane (E) or an image generated by a second image generator in a second image plane such that the user can perceive the image with the second eye (RA) when the holding device is placed on the head of the user, and/or in that the holding device carries a second refraction determining optical unit configured to determine the subjective refraction of the second eye (RA) when the holding device is placed on the head of the user.

6. The display device as claimed in claim 5, wherein the first imaging optical unit and the second imaging optical unit are configured complementarily to one another and/or in that the first refraction determining optical unit and the second refraction determining optical unit are configured complementarily to one another.

7. The display device as claimed in claim 1, wherein at least one of:
    an orientation sensor for determining an orientation of the holding device,
    a motion sensor for determining a movement of the holding device, or
    an inclination sensor for determining an inclination of the holding device,
        is mounted on the holding device.

8. The display device as claimed in claim 1, further comprising:
    a simulation unit for simulating an effect of a gaze of at least one of the first eye (LA) or the second eye (RA) of the user through a spectacle lens to be demonstrated for the at least one of the first eye (LA) or the second eye (RA);
    the simulation unit outputting the simulation of the effect of the gaze of the first eye (LA) of the user through the spectacle lens to be demonstrated for the first eye (LA) in the form of one image in the first image plane (E) generated by the first image generator, and/or
    the simulation unit outputting the simulation of the effect of the gaze of the second eye (RA) of the user through the spectacle lens to be demonstrated for the second eye (RA) in the form of one image in the first image plane (E) generated by the first image generator or in the form of one image in the second image plane generated by the second image generator.

9. The display device as claimed in claim 8, wherein at least one of:
    an orientation sensor for determining an orientation of the holding device,
    a motion sensor for determining a movement of the holding device, or
    an inclination sensor for determining an inclination of the holding device,
        is mounted on the holding device, and wherein
    the simulation unit is configured to take account of the orientation determined by the orientation sensor and/or the movement determined by the motion sensor and/or the inclination determined by the inclination sensor in the simulation of the effect of the gaze of the first eye (LA) of the user through the spectacle lens to be demonstrated for the first eye (LA), and/or
    the simulation unit is configured to take account of the orientation determined by the orientation sensor and/or the movement determined by the motion sensor and/or the inclination determined by the inclination sensor in the simulation of the effect of the gaze of the second eye (RA) of the user through the spectacle lens to be demonstrated for the second eye (RA).

10. The display device as claimed in claim 1, further comprising:
    an automatic variation unit being secured to the holding device,
    wherein the automatic variation unit is configured to vary at least one of the first imaging optical unit or the second imaging optical unit.

11. The display device as claimed in claim 10, wherein at least one of:
    an orientation sensor for determining an orientation of the holding device,
    a motion sensor for determining a movement of the holding device, or
    an inclination sensor for determining an inclination of the holding device,
        is mounted on the holding device, and wherein the automatic variation unit for varying the first imaging optical unit is configured to vary the first imaging optical unit on the basis of the orientation determined by the orientation sensor and/or on the basis of the movement determined by the motion sensor and/or on the basis of the inclination determined by the inclination sensor, and/or
    the automatic variation unit for varying the second imaging optical unit is configured to vary the second imaging optical unit on the basis of the orientation determined by the orientation sensor and/or on the basis of the movement determined by the motion sensor and/or on the basis of the inclination determined by the inclination sensor.

12. The display device as claimed claim 1, wherein
    a first viewing direction determining unit is provided on the holding device to determine the direction of the gaze of the first eye (LA), and/or
    a second viewing direction determining unit is provided on the holding device to determine the direction of the gaze of the second eye (RA).

13. The display device as claimed in claim 12, wherein
    the simulation unit is configured to take account of the direction of the gaze of the first eye (LA), the direction being determined by the first viewing direction determining unit, in the simulation, and/or
    the simulation unit is configured to take account of the direction of the gaze of the second eye (RA), the direction being determined by the second viewing direction determining unit, in the simulation.

14. The display device as claimed in claim 12, wherein
    the automatic variation unit for varying the first imaging optical unit is configured to vary the first imaging optical unit on the basis of the direction of the gaze of the first eye (LA), the direction being determined by the first viewing direction determining unit, and/or
    the automatic variation unit for varying the second imaging optical unit is configured to vary the second imaging optical unit on the basis of the direction of the gaze of the second eye (RA), the direction being determined by the second viewing direction determining unit.

15. The display device as claimed in claim 1, wherein
    the holding device carries a first camera having an optical axis, the camera being controlled by the viewing direction of the first eye such that the optical axis of the first camera and an optical axis running in the viewing direction of the first eye (LA) through the pupil center of the first eye (LA) correspond, and the holding device carries a first distance sensor arranged such that the first distance sensor detects a distance to an object recorded by the first camera in the form of a camera image, and
    the simulation unit for simulating the effect of a gaze of the first eye (LA) of the user through a spectacle lens to be demonstrated for the first eye (LA) is configured to simulate the image generated by the first image generator in the first image plane (E) from the camera image recorded by the first camera and from the distance detected by the first distance sensor; and/or the holding device carries a second camera having an optical axis, the camera being controlled by the viewing direction of the second eye (RA) such that the optical axis of the second camera and an optical axis running in the viewing direction of the second eye through the pupil center of the second eye (RA) correspond, and the holding device carries a second distance sensor arranged such that the second distance sensor detects a distance to an object recorded by the second camera in the form of a camera image, and the simulation unit for simulating the effect of a gaze of the second eye (RA) of the user through a spectacle lens to be demonstrated for the second eye (RA) is configured to simulate the image generated by the image generator in the first image plane (E) and/or the image generated by the second image generator in the second image plane (E') from the camera image recorded by the second camera and from the distance detected by the second distance sensor.

16. A system comprising a display device as claimed in claim 1 and a manual operating unit for driving at least one of:
   the first refraction determining optical unit,
   the first imaging optical unit, or
   the simulation unit.

17. A system comprising a first image generator and a holding device which can be placed onto the head of a user, the system comprising:
   a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user,
   wherein the holding device carries a first refraction determining optical unit configured to determine the subjective refraction of the first eye (LA) when the holding device is placed on the head of the user;
   wherein the first refraction determining optical unit includes two measuring spectacle lenses displaceable relative to one another in the form of Alvarez lenses, or
   wherein the first refraction determining optical unit includes a lens having a plurality of adjacent first zones arranged over the lens in a first direction,
      wherein each first zone has a different average power, wherein a plurality of adjacent second zones are arranged over the first lens in a second direction perpendicular to the first direction,
      wherein each second zone has a different cylinder power,
      wherein the first zones arranged over the first lens in the first direction overlap the second zones arranged over the first lens in the second direction,
      wherein the lens is configured to be rotatable and/or displaceable parallel to the first image plane (E), and
      wherein the first imaging optical unit is arranged between the first image plane (E) and the first refraction determining optical unit.

18. The system as claimed in claim 17, wherein the first imaging optical unit is configured to be variable.

19. The system as claimed in claim 17, further comprising:
   a second imaging optical unit configured to be variable and being secured to the holding device,
   the second imaging optical unit being configured to image the image generated in the first image plane such that the user can perceive the image with the second eye (RA) when the holding device is placed on the head of the user, and/or
   the holding device carries a second refraction determining optical unit configured to determine the subjective refraction of the second eye (RA) when the holding device is placed on the head of the user, and
   an image separating system being configured to feed first image contents of the image generated in the image plane (E) exclusively to the first eye (LA) and second image contents, deviating from the first image contents, exclusively to the second eye (RA).

20. A display device comprising:
   a holding device that can be placed onto the head of a user;
      a first image generator secured to the holding device and configured to generate an image in a first image plane (E), or
      a receptacle for receiving the first image generator such that the first image plane (E), in which the image of the first image generator is generated, is arranged in a predetermined position in relation to the holding device;
   a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user; and
   at least one of:
   an orientation sensor for determining an orientation of the holding device,
   a motion sensor for determining a movement of the holding device, or
   an inclination sensor for determining an inclination of the holding device,
      being mounted on the holding device,
   wherein the holding device carries a first refraction determining optical unit configured to determine the subjective refraction of the first eye (LA) when the holding device is placed on the head of the user, and
   wherein the first imaging optical unit is arranged between the first image plane (E) and the first refraction determining optical unit.

21. A display device comprising:
   a holding device that can be placed onto the head of a user;
      a first image generator secured to the holding device and configured to generate an image in a first image plane (E), or
      a receptacle for receiving the first image generator such that the first image plane (E), in which the image of the first image generator is generated, is arranged in a predetermined position in relation to the holding device;
      a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user; and a simulation unit for simulating an effect of a gaze of at least one of the first eye (LA) or a second eye (RA) of the user through a spectacle lens to be demonstrated for the at least one of the first eye (LA) or the second eye (RA); wherein
the simulation unit outputting the simulation of the effect of the gaze of the first eye (LA) of the user through the spectacle lens to be demonstrated for the first eye (LA) in the form of one image in the first image plane (E) generated by the first image generator, and/or
the simulation unit outputting the simulation of the effect of the gaze of the second eye (RA) of the user through the spectacle lens to be demonstrated for the second eye (RA) in the form of one image in the first image plane (E) generated by the first image generator or in the form of one image in the second image plane generated by the second image generator,
wherein the holding device carries a first refraction determining optical unit configured to determine the subjective refraction of the first eye (LA) when the holding device is placed on the head of the user, and
wherein the first imaging optical unit is arranged between the first image plane (E) and the first refraction determining optical unit.

22. A display device comprising:
a holding device that can be placed onto the head of a user;
  a first image generator secured to the holding device and configured to generate an image in a first image plane (E), or
  a receptacle for receiving the first image generator such that the first image plane (E), in which the image of the first image generator is generated, is arranged in a predetermined position in relation to the holding device;
  a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user; and
  a simulation unit for simulating an effect of a gaze of at least one of the first eye (LA) or a second eye (RA) of the user through a spectacle lens to be demonstrated for the at least one of the first eye (LA) or the second eye (RA); wherein
    the simulation unit outputting the simulation of the effect of the gaze of the first eye (LA) of the user through the spectacle lens to be demonstrated for the first eye (LA) in the form of one image in the first image plane (E) generated by the first image generator, and/or
    the simulation unit outputting the simulation of the effect of the gaze of the second eye (RA) of the user through the spectacle lens to be demonstrated for the second eye (RA) in the form of one image in the first image plane (E) generated by the first image generator or in the form of one image in the second image plane generated by the second image generator; and wherein
    the simulation unit is configured to take account of the orientation determined by the orientation sensor and/or the movement determined by the motion sensor and/or the inclination determined by the inclination sensor in the simulation of the effect of the gaze of the first eye (LA) of the user through the spectacle lens to be demonstrated for the first eye (LA), and/or
    the simulation unit is configured to take account of the orientation determined by the orientation sensor and/or the movement determined by the motion sensor and/or the inclination determined by the inclination sensor in the simulation of the effect of the gaze of the second eye (RA) of the user through the spectacle lens to be demonstrated for the second eye (RA),
  wherein the holding device carries a first refraction determining optical unit configured to determine the subjective refraction of the first eye (LA) when the holding device is placed on the head of the user, and
  wherein the first imaging optical unit is arranged between the first image plane (E) and the first refraction determining optical unit.

23. A display device comprising:
a holding device that can be placed onto the head of a user;
  a first image generator secured to the holding device and configured to generate an image in a first image plane (E), or
  a receptacle for receiving the first image generator such that the first image plane (E), in which the image of the first image generator is generated, is arranged in a predetermined position in relation to the holding device; and
a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user;
wherein the holding device carries a first refraction determining optical unit configured to determine a subjective refraction of the first eye (LA) when the holding device is placed on the head of the user,
  wherein the first refraction determining optical unit has two measuring spectacle lenses displaceable relative to one another in the form of Alvarez lenses, or
  wherein the first refraction determining optical unit includes a lens having a plurality of adjacent first zones arranged over the lens in a first direction, wherein each first zone has a different average power, where a plurality of adjacent second zones is arranged over the first lens in a second direction perpendicular to the first direction, wherein each second zone has a different cylinder power, wherein the first zones arranged over the first lens in the first direction overlap the second zones arranged over the first lens in the second direction, and wherein the lens is configured to be rotatable, displaceable, or rotatable and displaceable parallel to the first image plane (E);
wherein the first imaging optical unit includes at least one imaging lens arranged between the image generated by the first image generator in the first image plane (E) and the first eye (LA) when the holding device is placed on the head of the user, and
wherein the first imaging optical unit is arranged between the first image plane (E) and the first refraction determining optical unit.

24. A system comprising a first image generator and a holding device which can be placed onto the head of a user, the system comprising:
- a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user, wherein the holding device carries a first refraction determining optical unit configured to determine the subjective refraction of the first eye (LA) when the holding device is placed on the head of the user;
- wherein the first refraction determining optical unit includes two measuring spectacle lenses displaceable relative to one another in the form of Alvarez lenses, or
- wherein the first refraction determining optical unit includes a lens having a plurality of adjacent first zones arranged over the lens in a first direction,
  - wherein each first zone has a different average power, wherein a plurality of adjacent second zones are arranged over the first lens in a second direction perpendicular to the first direction,
  - wherein each second zone has a different cylinder power,
  - wherein the first zones arranged over the first lens in the first direction overlap the second zones arranged over the first lens in the second direction,
  - wherein the lens is configured to be rotatable and/or displaceable parallel to the first image plane (E),
  - wherein at least one of:
    - an orientation sensor for determining an orientation of the holding device,
    - a motion sensor for determining a movement of the holding device, or
    - an inclination sensor for determining an inclination of the holding device, is mounted on the holding device, and
- wherein the first imaging optical unit is arranged between the first image plane (E) and the first refraction determining optical unit.

25. A system comprising a first image generator and a holding device which can be placed onto the head of a user, the system comprising:
- a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user, wherein the holding device carries a first refraction determining optical unit configured to determine the subjective refraction of the first eye (LA) when the holding device is placed on the head of the user;
- wherein the first refraction determining optical unit includes two measuring spectacle lenses displaceable relative to one another in the form of Alvarez lenses, or
- wherein the first refraction determining optical unit includes a lens having a plurality of adjacent first zones arranged over the lens in a first direction,
  - wherein each first zone has a different average power, wherein a plurality of adjacent second zones are arranged over the first lens in a second direction perpendicular to the first direction,
  - wherein each second zone has a different cylinder power,
  - wherein the first zones arranged over the first lens in the first direction overlap the second zones arranged over the first lens in the second direction,
  - wherein the lens is configured to be rotatable and/or displaceable parallel to the first image plane (E);
- a simulation unit for simulating an effect of a gaze of at least one of the first eye (LA) or the second eye (RA) of the user through a spectacle lens to be demonstrated for the at least one of the first eye (LA) or the second eye (RA);
  - the simulation unit outputting the simulation of the effect of the gaze of the first eye (LA) of the user through the spectacle lens to be demonstrated for the first eye (LA) in the form of one image in the first image plane (E) generated by the first image generator, and/or
  - the simulation unit outputting the simulation of the effect of the gaze of the second eye (RA) of the user through the spectacle lens to be demonstrated for the second eye (RA) in the form of one image in the first image plane (E) generated by the first image generator or in the form of one image in the second image plane generated by the second image generator, and
- wherein the first imaging optical unit is arranged between the first image plane (E) and the first refraction determining optical unit.

26. A system comprising a first image generator and a holding device which can be placed onto the head of a user, the system comprising:
- a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user, wherein the holding device carries a first refraction determining optical unit configured to determine the subjective refraction of the first eye (LA) when the holding device is placed on the head of the user;
- wherein the first refraction determining optical unit includes two measuring spectacle lenses displaceable relative to one another in the form of Alvarez lenses, or
- wherein the first refraction determining optical unit includes a lens having a plurality of adjacent first zones arranged over the lens in a first direction,
  - wherein each first zone has a different average power, wherein a plurality of adjacent second zones are arranged over the first lens in a second direction perpendicular to the first direction,
  - wherein each second zone has a different cylinder power,
  - wherein the first zones arranged over the first lens in the first direction overlap the second zones arranged over the first lens in the second direction,
  - wherein the lens is configured to be rotatable and/or displaceable parallel to the first image plane (E),
  - wherein at least one of:
    - an orientation sensor for determining an orientation of the holding device, a motion sensor for determining a movement of the holding device, or an inclination sensor for determining an inclination of the holding device, is mounted on the holding device, and wherein the first imaging optical unit is arranged between the first image plane (E) and the first refraction determining optical unit.

27. A system comprising a first image generator and a holding device which can be placed onto the head of a user, the system comprising:

a first imaging optical unit secured to the holding device and configured to display an image generated by the first image generator in the first image plane (E) such that the user can perceive with a first eye (LA) the image generated by the first image generator and displayed with the first imaging optical unit when the holding device is placed on the head of the user, wherein the holding device carries a first refraction determining optical unit configured to determine the subjective refraction of the first eye (LA) when the holding device is placed on the head of the user;

wherein the first refraction determining optical unit includes two measuring spectacle lenses displaceable relative to one another in the form of Alvarez lenses, or wherein the first refraction determining optical unit includes a lens having a plurality of adjacent first zones arranged over the lens in a first direction, wherein each first zone has a different average power, wherein a plurality of adjacent second zones are arranged over the first lens in a second direction perpendicular to the first direction, wherein each second zone has a different cylinder power, wherein the first zones arranged over the first lens in the first direction overlap the second zones arranged over the first lens in the second direction, and wherein the lens is configured to be rotatable and/or displaceable parallel to the first image plane (E), wherein the first imaging optical unit includes at least one imaging lens arranged between the image generated by the first image generator in the first image plane (E) and the first eye (LA) when the holding device is placed on the head of the user, and wherein the first imaging optical unit is arranged between the first image plane (E) and the first refraction determining optical unit.

\* \* \* \* \*

UNITED STATES PATENT AND TRADEMARK OFFICE
CERTIFICATE OF CORRECTION

PATENT NO. : 10,292,581 B2
APPLICATION NO. : 15/462810
DATED : May 21, 2019
INVENTOR(S) : Manfred Arnold et al.

Page 1 of 1

It is certified that error appears in the above-identified patent and that said Letters Patent is hereby corrected as shown below:

In the Claims

Column 26, Lines 66 to 67: delete "in that" and insert -- wherein -- therefor.

Column 27, Line 6: delete "in that" and insert -- wherein -- therefor.

Signed and Sealed this
Twentieth Day of August, 2019

Andrei Iancu
*Director of the United States Patent and Trademark Office*